(12) United States Patent
Neumann

(10) Patent No.: US 10,004,469 B2
(45) Date of Patent: Jun. 26, 2018

(54) FLAT PANEL X-RAY IMAGING DEVICE—TWIN FLAT DETECTOR SIGNAL SYNCHRONIZATION

(71) Applicant: SCANFLEX HEALTHCARE AB, Stockholm (SE)

(72) Inventor: Volker Neumann, Hamburg (DE)

(73) Assignee: SCANFLEX HEALTHCARE AB, Stockholm (SE)

( * ) Notice: Subject to any disclaimer, the term of this patent is extended or adjusted under 35 U.S.C. 154(b) by 0 days. days.

(21) Appl. No.: 15/037,751

(22) PCT Filed: Nov. 19, 2014

(86) PCT No.: PCT/SE2014/051386
§ 371 (c)(1),
(2) Date: May 19, 2016

(87) PCT Pub. No.: WO2015/076743
PCT Pub. Date: May 28, 2015

(65) Prior Publication Data
US 2016/0287200 A1 Oct. 6, 2016

Related U.S. Application Data

(60) Provisional application No. 61/906,028, filed on Nov. 19, 2013.

(51) Int. Cl.
*A61B 19/00* (2006.01)
*A61B 6/00* (2006.01)
*H05G 1/32* (2006.01)

(52) U.S. Cl.
CPC ............ *A61B 6/487* (2013.01); *A61B 6/4014* (2013.01); *A61B 6/4233* (2013.01);
(Continued)

(58) Field of Classification Search
None
See application file for complete search history.

(56) References Cited

U.S. PATENT DOCUMENTS 5,835,557 A 11/1998 Malmstroem
5,923,721 A 7/1999 Duschka
(Continued)

FOREIGN PATENT DOCUMENTS

CN 102961157 A 3/2013

*Primary Examiner* — Hoon Song
(74) *Attorney, Agent, or Firm* — Gabriela B. Tomescu, Esq.; Bergenstahle & Partners AB

(57) ABSTRACT

A mobile digital fluoroscopy system comprising a mobile X-ray system carrier unit (1) comprising a first and a second X-ray device (19, 20) each having a transmitter (21, 23) and a receiver (22, 24), wherein said respective first and second X-ray devices (19, 20) are configured to enable X-ray imaging in mutually intersecting planes, a kV unit 1012; and; wherein said a mobile control unit (2a) is communicatively coupled to the mobile X-ray system carrier (1) via a cable (150), wherein said mobile control unit (2a) is configured to receive a first set of image data 810 from said kV unit (1012) and sending a control signal to said kV unit (1012) upon completion of receiving of said image data 810, wherein kV unit 1012 is configured to generate a synchronization signal 820 to said transmitters (21, 23) and receivers (22,24) and to send a second set of image data 810 received from receivers (22,24) to the mobile control unit 2a.

8 Claims, 17 Drawing Sheets

(52) U.S. Cl.
CPC .......... *A61B 6/4266* (2013.01); *A61B 6/4405* (2013.01); *A61B 6/4441* (2013.01); *A61B 6/4482* (2013.01); *A61B 6/463* (2013.01); *A61B 6/542* (2013.01); *A61B 6/545* (2013.01); *A61B 6/56* (2013.01); *A61B 6/467* (2013.01); *H05G 1/32* (2013.01)

(56) References Cited

U.S. PATENT DOCUMENTS

| | | | | |
|---|---|---|---|---|
| 6,104,780 | A * | 8/2000 | Hanover | A61B 6/4014 378/101 |
| 7,806,589 | B2 * | 10/2010 | Tashman | A61B 5/1038 378/193 |
| 2005/0116878 | A1 | 6/2005 | Warnberg | |
| 2010/0249800 | A1 | 9/2010 | Kim | |
| 2011/0129067 | A1 * | 6/2011 | Fukuwara | A61B 6/4014 378/115 |

* cited by examiner

X radiating plane img
S scattered plane img
D dark planes img

FLAT PANEL X-RAY IMAGING DEVICE—TWIN FLAT DETECTOR SIGNAL SYNCHRONIZATION

FIELD OF THE INVENTION

The present invention relates in general to a preferably mobile digital fluoroscopy system for medical applications operating with an X-ray device mounted to generate X-ray images.

More specifically, the present invention relates to signal synchronization of emitting X-ray radiation pulses and of capturing images receivers in a fluoroscopy system having multiple X-ray devices each provided with a flat digital X-ray detector, and oriented on different axes to provide different views of the location of interest in the patient with the ability to control the area of the patient exposed to the X-ray beam via a user interface.

BACKGROUND

In orthopedic surgery environment, there is a need for allowing full access to the operating area with total control at each step. Therefore, X-ray imaging using C-stands or G-stands comprising imaging systems is commonly used, wherein a C-stand only has one X-ray imaging device while a so-called G-stand comprises two such imaging devices, with their axes oriented at an angle to each other.

A symmetrical G-stand is generally preferable to a C-stand, since it comprises two perpendicularly mounted X-ray imaging devices, and is thereby able to provide both frontal and lateral X-ray imaging with fixed settings. The ability to simultaneously see the surgical area in both a frontal and lateral view reduces the need to move and adjust the equipment during surgery, thus reducing both surgery time and radiation dose. When the need to move the equipment is reduced, better sterility is also achieved.

The ability in a G-stand to double the surgeon's view also results in accurate positioning of implants, creating a safer and more reliable method of surgery. The X-ray devices are fixed in perpendicular relation to each other in the G-stand, but the entire G-stand can be tilted somewhat for better access and views. Or in some G-stand systems, the G-stand is somewhat rotatable about a horizontal axis perpendicular to the axes of both of the X-ray devices.

SUMMARY OF THE INVENTION

The general object of the invention is to provide improvements in a digital fluoroscopy system for medical applications operating with first and second X-ray imaging devices configured, e.g. by being mounted on a G-stand, to generate X-ray images along two mutually intersecting axes.

A problem with conventional systems is that the value of voltage in kV to energize the X-ray generators for emitting energy as needed in the scan process in order to achieve an as efficient scan as possible is not provided and is not easily determined without time lost in order to calibrate the system. It is also not intuitive or easily determined how much more added or how much reduced kV is needed in order to have a successful scan. Another problem is connecting the complex systems without having the carrier of the X-ray systems, e.g. in the form of a G-arm, being too bulky or heavy or with too many cables connecting the apparatus to the control unit and displays.

One embodiment of the invention solves this narrowing the area of interest by having an overview of the regulated kV value dependent on previous output and regulating a pulse width, the result is a well regulated and controlled kV output which the user can view and adjust accordingly if needed. By having an adaption unit 120 connecting the various embodiments of the systems results in less cables being needed. In one embodiment, a mobile digital fluoroscopy system, having a mobile X-ray system carrier unit having a first and a second X-ray system each having a transmitter and a receiver, said respective first and second X-ray systems being configured, e.g. by being mounted on a G-arm, to enable X-ray imaging in mutually intersecting planes.

In one embodiment the system further comprises:
a mobile control unit 200 configured to receive a control voltage value via a control interface and send said control voltage value to a monoblock 230 configured to measure a voltage used in the system and sending said measured voltage value 291 to a kV unit 250;
a kV unit 250 configured to receive a measured voltage value from said monoblock 230, calculates a regulated voltage value based on said measured voltage value 291 and
sending said regulated voltage value to inverter 240;
an inverter unit 240 configured to generate a voltage value 290 to monoblock 230 based on and corresponding to said regulated voltage value received from kV unit 250.

In one embodiment, a computer program product comprising computer readable code configured to, when executed in a processor, perform any or all of the method steps described herein.

In one embodiment, a non-transitory computer readable memory on which is stored computer readable code configured to, when executed in a processor, perform any or all of the method steps described herein.

Another problem with the conventional systems is that the system requires a large amount of cables, thereby increasing cost and complexity of the system, decreasing the mobility of the system and increasing the risk of personnel involved tripping or disconnecting a cord during operation of the system.

A further problem is that since the first and second X-ray imaging devices are mounted on the G-stand to generate X-ray images along two mutually intersecting axes the images captured by one of the X-ray imaging devices are typically noisy, due to interference between X-ray radiation emitted along the first plane and X-ray radiation emitted along the second plane.

According to various embodiments, these problems are solved by methods and systems comprising synchronization the signal communication between the first and second X-ray devices 19, 20 and the mobile control unit 2a, as further described herein.

One embodiment of the inventive concept is a mobile digital fluoroscopy system comprising:
a mobile X-ray system carrier unit 1 comprising;
a first and a second X-ray device 19, 20 each having a transmitter 21, 23 and a receiver 22, 24, wherein said respective first and second X-ray devices 19, 20 are configured to enable X-ray imaging in mutually intersecting planes,
a kV unit 1012; and wherein said a mobile control unit 2a is communicatively coupled to the mobile X-ray system carrier 1 via a cable 150;
wherein said mobile control unit 2a is configured to receive a first set of image data 810 from said kV unit 1012 and sending a control signal to said kV unit 1012 upon completion of receiving of said image data 810;

wherein kV unit 1012 is configured to generate a synchronization signal 820 to said transmitters 21, 23 and receivers 22, 24 and to send a second set of image data 810 received from receivers 22, 24 to the mobile control unit 2a.

Another embodiment of the inventive concept a method in a mobile digital fluoroscopy system comprising:
a mobile X-ray system carrier unit 1 comprising;
a first and a second X-ray device 19, 20 each having a transmitter 21, 23 and a receiver 22, 24, wherein said respective first and second X-ray devices 19, 20 are configured to enable X-ray imaging in mutually intersecting planes,
a kV unit 1012; and;
wherein said a mobile control unit 2a is communicatively coupled to the mobile X-ray system carrier 1 via a cable 150, the method comprise:
receiving a first set of image data 810, by mobile control unit 2a, from said kV unit 1012,
sending, by mobile control unit 2a, a control signal to said kV unit 1012 upon completion of receiving of said image data 810,
generating a synchronization signal 820 to said transmitters 21, 23 and receivers 22, 24;
sending image data 810 received from receivers 22, 24 to the mobile control unit 2a.

Further embodiments of the inventive concept are described in the claims and the below description.

BRIEF DESCRIPTION OF THE DRAWINGS

The present invention will be further explained below with reference to the accompanying drawings, in which:

FIG. 14 shows an embodiment of a method in fluoroscopy system for synchronizing of emitting X-ray radiation pulses, of capturing images receivers and of transferring image data from the X-ray system carrier unit 1 to the mobile control unit 2a.

DETAILED DESCRIPTION OF THE INVENTION

System Overview

Figure 1A:
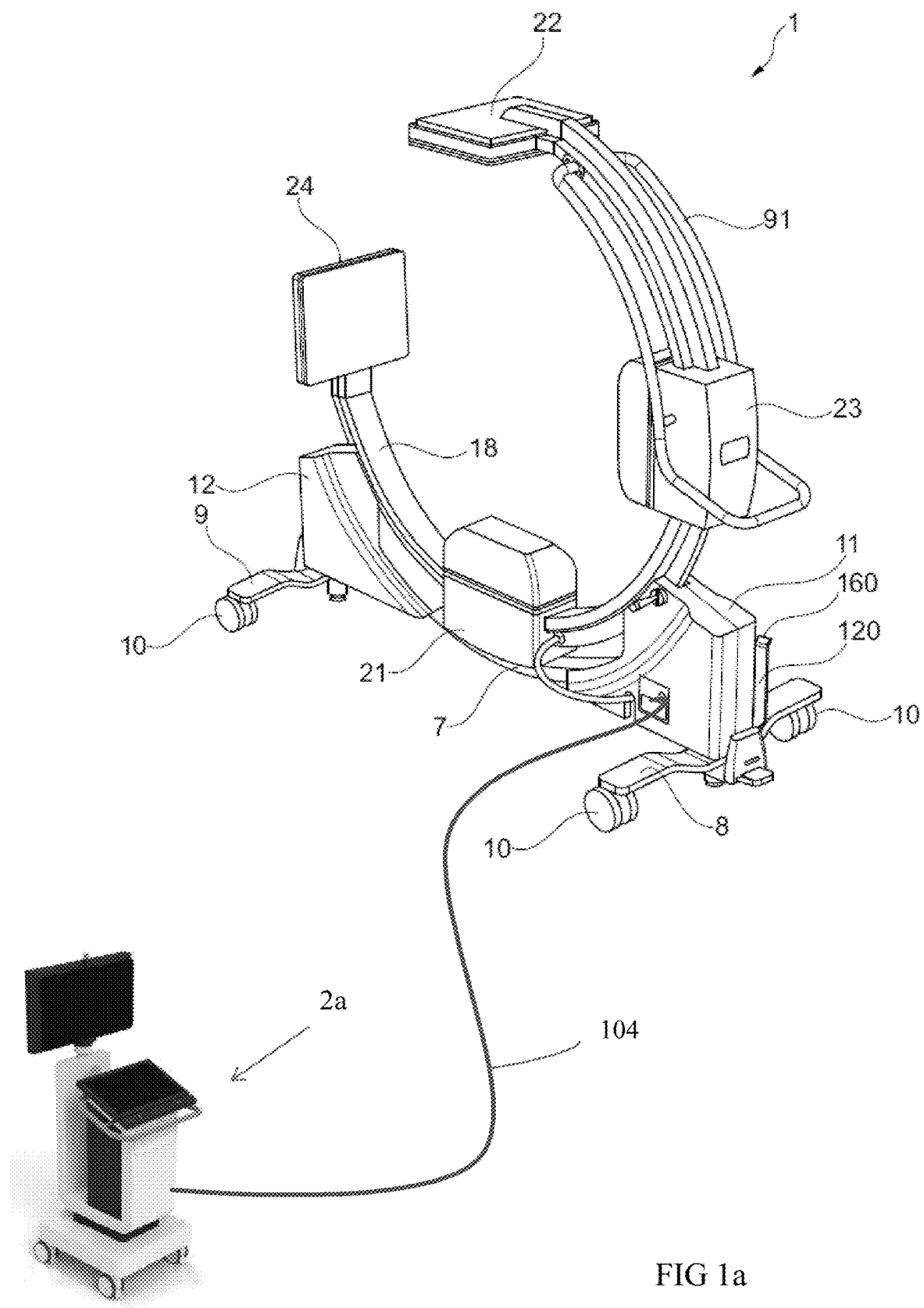
FIG. 1a and FIG. 1b shows a schematic overview of an exemplifying system embodiments of the invention in a digital fluoroscopy system configured on a G-arm on a mobile G-stand coupled to a mobile control unit.

The present invention concerns an X-ray apparatus configured as a system of components illustrated in the Figures of the drawings, adapted for use in connection with surgical orthopedic operations.

Embodiments of the invention comprise a mobile G-arm fluoroscopy system provided with flat digital X-ray detectors.

According to an embodiment, there is provided a mobile digital fluoroscopy system, comprising a mobile unit 1, also called a mobile X-ray system carrier unit 1, having a stand having a G-arm 18 suspended on a chassis frame 7; a first X-ray device 19 mounted on the G-arm 18 to transmit an X-ray beam along a first plane P1, the first X-ray device 19 having a first receiver 22 mounted on the G-arm 18 and a first transmitter 21 mounted on the G-arm 18 opposite said first receiver 22; a second X-ray device 20 mounted on the G-arm 18 to transmit an X-ray beam along a second plane P2 intersecting the first axis P1 of the first X-ray device, the second X-ray device 20 having a second receiver 24 In an embodiment, the X-ray system carrier unit 1 further comprises a kV unit 1020 configured to generate a synchronization signal 820 to said transmitters 21, 23 and receivers 22, 24 and to send a second set of image data 810 received from receivers 22, 24 to the mobile control unit 2a, wherein the synchronization signal 820 is configured to control timing of the first and/or second transmitter to emit/not to emit X-ray energy based on said synchronization signal 820 and to control timing of said first receiver 22 and said second receiver 24 to capture and send a second set of image data to said kV unit 1012. In an embodiment, the first and second receivers 22 and 24 are image intensifiers, according to any configuration known in the art, mounted at respective ends of the G-arm. In an embodiment, said first and second receivers 22 and 24 are flat digital X-ray detectors.

Figure 1B:
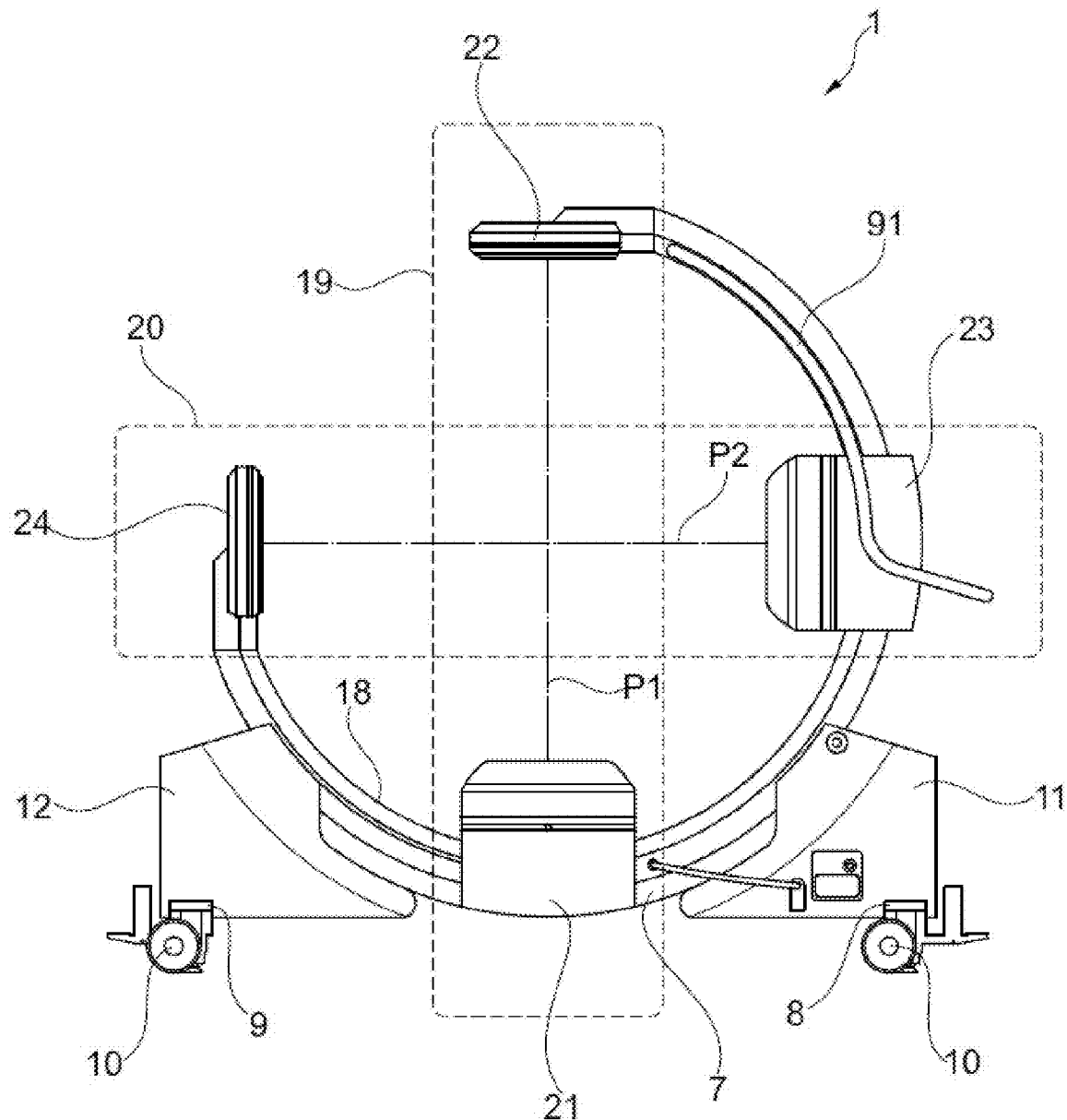

The apparatus shown in FIG. 1a and FIG. 1b comprises a mobile unit 1, i.e. a mobile X-ray system carrier unit 1 provided with two X-ray systems 19, 20 mounted to operate and transmit X-ray beams along mutually intersecting axes P1, P2. The arm 18 of the embodiment illustrated in FIG. 1a and FIG. 1b is referred to as a G-arm.

An object, typically the body of a patient undergoing surgery, is placed inside the mobile unit 1 so that beam axis P1 and beam axis P2 of the two X-ray systems cross within the object. The first X-ray device 19 includes a first transmitter 21 (an X-ray tube or x-tube) for emitting X-rays and a first receiver 22 (e.g. image intensifier or semiconductor sensors) for receiving X-rays emitted by the first transmitter 21 and having passed through the object. The first transmitter 21 may be located down below on the arm 18 and the first receiver 22 at the top of the arm 18. The second X-ray device 20 includes a second transmitter 23 (an X-ray tube or x-tube) for emitting X-rays and a second receiver 24 (e.g. image intensifier or semiconductor sensors) for receiving X-rays emitted by the second transmitter 23 and having passed through said object. The receivers 22, 24 may each comprise image intensifying means and an image capturing device, typically a CCD camera, for converting X-rays into a visible image.

FIG. 1a and FIG. 1b shows a G-arm to be placed around the patient together with a separate console 2a which can be operated by the surgeon prior to the operation or during the operation by an assistant who does not have sterility restraints. High definition monitors 4a face the surgeon displaying the X-ray images in two different orthogonal planes either in real time or in so called "cine" replay to review exactly how and precisely where a prosthetic joint component has been placed without the necessity of exposing the patient and surgeon to ore X-ray radiation.

An embodiment of a mobile control unit 2a, also called console 2a, is provided with a base module 106 on wheels, a pulpit stand module 108 having a larger main part and a back part with a slot 5 in between. An operator control interface in the form of a touch screen 3b devised for presentation of one or more graphical user interfaces and a physical button panel 116 are mounted on the main part of the pulpit stand module to form a lectern like control panel, in this example also comprising a handle 118 configured for gripping when moving around the console and for resting to support ergonomic operation of the control interface. The back part of the pulpit stand module is configured for mounting display monitors or screens for presenting X-ray images.

Figure 2:
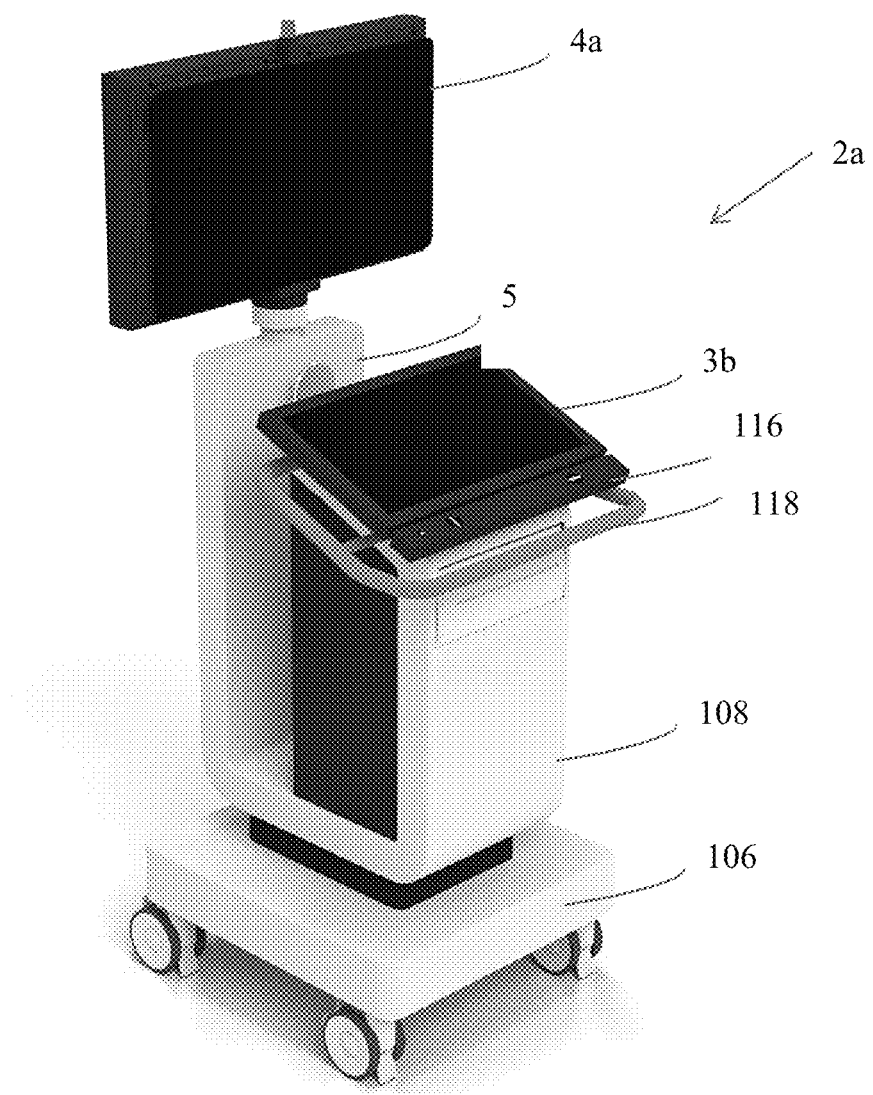
FIG. 2 shows a schematic view of an exemplifying embodiment of a mobile control unit.
Figure 3:
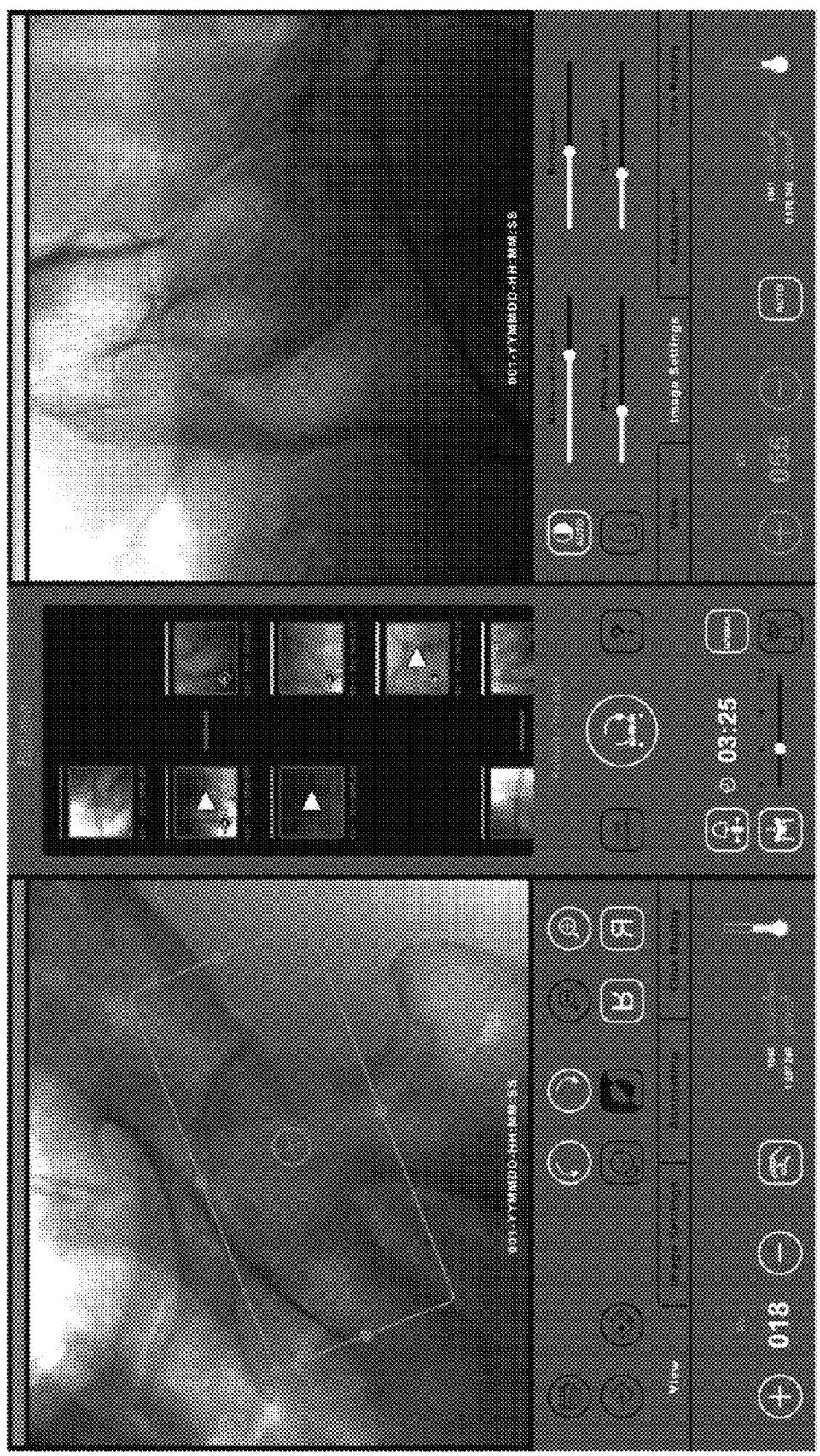
FIG. 3 shows a schematic first view of an exemplifying embodiment of a graphical user interface GUI implemented in the mobile control unit.
Figure 4:
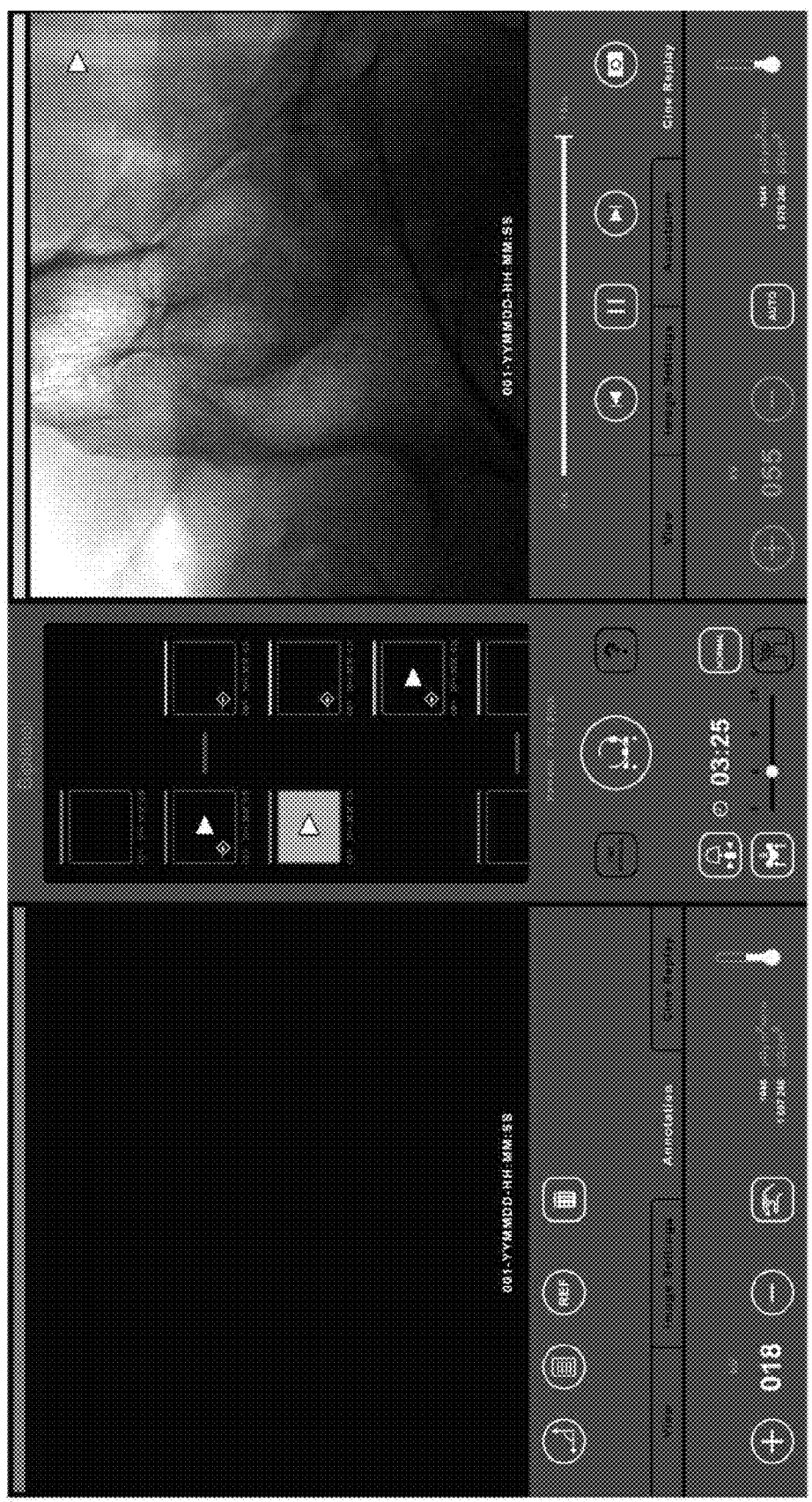
FIG. 4 shows a schematic second view of an exemplifying embodiment of a graphical user interface GUI implemented in the mobile control unit.

The HD display monitors 4b can be turned to face the operator of the console or can be turned to face a different direction. During an operation, the high definition monitors will typically be turned around to present the fluoroscopic images to the surgeon. The cables 104 connecting the G-stand to the console can be wound up and stored in the slot 5 when the console and the G-stand are close to each other. The console shown in FIG. 2 has a touch screen graphic user interface (GUI) 3b, comprising in this case two fields which can be configured in various ways as shown in FIGS. 3-4. FIG. 3 for example shows horizontal and vertical x-ray views of a prosthesis mounted in a patient's hip, each view being surrounded by touch screen button or slide controls as well as numerical or analogue read-outs. The GUI may be presented with a configuration in which the left half of the touchscreen has a keyboard for inputting and recording information to identify patient or operation information for example and "cine" recordings.

Such a system may in addition to comprising high resolution monitors for presenting images to a surgeon for example also comprise components such as a foot switch (not shown) to enable the surgeon with sterile hands to switch between images taken in the respective planes. The control unit preferably further comprises at least one touch screen display for displaying image data, a control panel, and a data processor comprising image processing means adapted to receive images transmitted from said image capturing devices comprised in said receivers 22, 24. The mobile unit 1a and the control unit 2a are communicatively coupled to each other, for instance by means of a cable or through wireless signal transmission.

The control unit is further configured to receive user indications via said touch screen as user input data in the form of user input data signals, to process user input data to control data indicative of a desired adjustments of functions in system, to send said control data as control signals to such functions, to receive functional status data as status control signals from a respective functions, to process function status data to a visual representation of said function status data and to send said visual representation to said touch screen as a display signal, wherein said touch screen is configured to display said visual representation to a user.

The control unit further comprises a processor/processing unit 910 provided with specifically designed programming or program code portions configured to control the processing unit to perform the steps and functions of embodiments of the inventive method described herein. The control unit further comprises at least one memory 930 configured to store data values or parameters received from a processor 910 or to retrieve and send data values or parameters to a processor 910. The control unit further comprises a communications interface 940 configured to send or receive data values or parameters to/from a processor 910 to/from external units via the communications interface 940.

Figure 8:
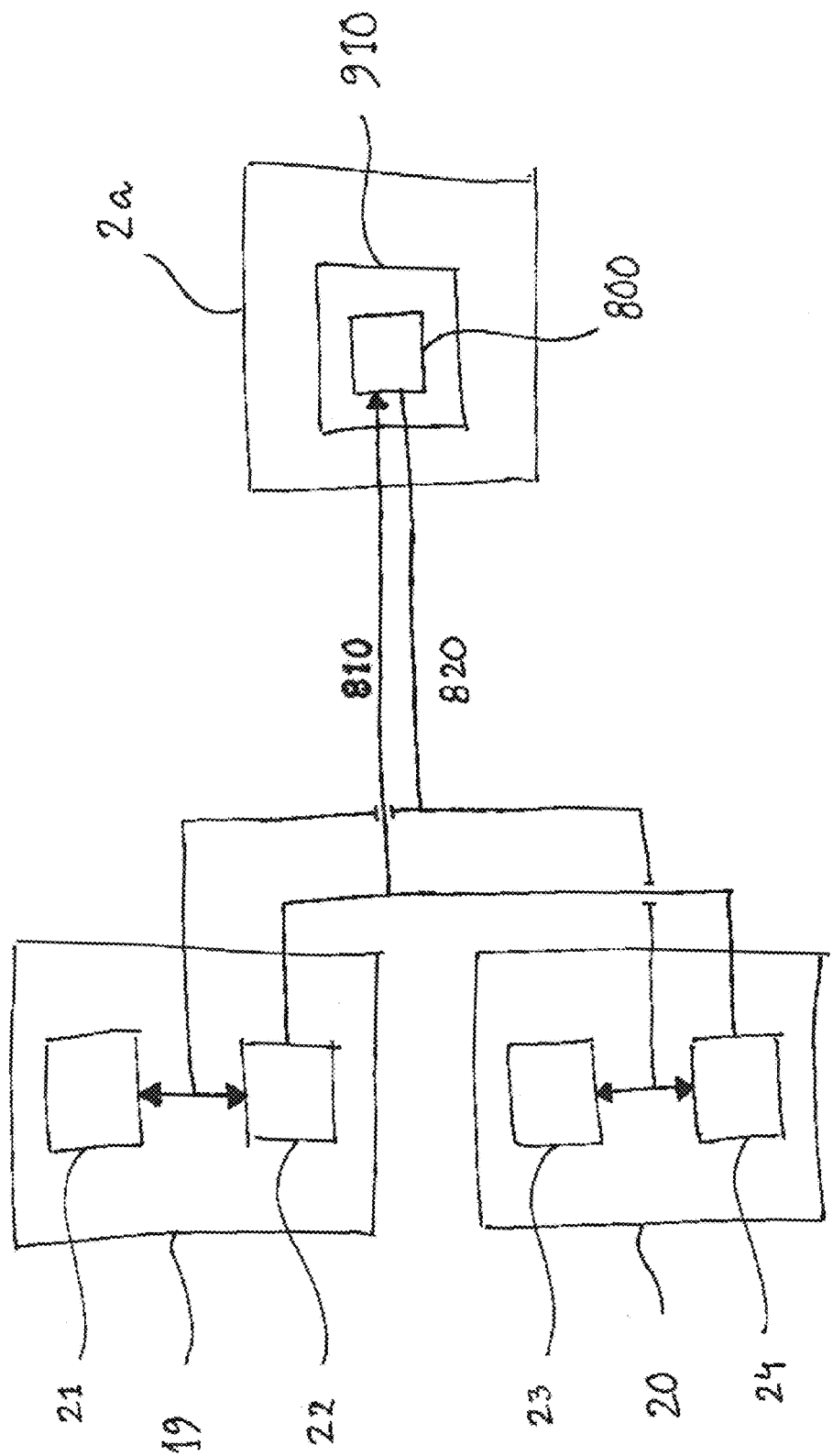
FIG. 8 shows a schematic overview of synchronization of the signal communication of the digital fluoroscopy system, according to embodiments of the invention.

In embodiments shown in the schematic overview of FIG. 8, a synchronization unit 800 is integrated in, implemented in or communicatively coupled to the processor 910. In yet an embodiment, a synchronization unit 800 is integrated in, implemented in or communicatively coupled to the kV unit 1012. The synchronization unit 800 is configured to synchronize the signal communication between the first and second X-ray devices 19, 20 and the mobile control unit 2a.

In embodiments, there is provided a mobile digital fluoroscopy system, comprising: a mobile X-ray system carrier unit 1 having a first and a second X-ray device 19, 20 each having a transmitter 21, 23 and a receiver 22, 24, said respective first and second X-ray devices 19, 20 being mounted on a G-arm 18 to enable X-ray imaging in mutually intersecting planes; a mobile control unit 2a, wherein the mobile X-ray system carrier 1 is communicatively coupled to the mobile control unit 2a; a processor 910 implemented in said mobile control unit 2a or in a kV unit 1020; and a synchronizing unit 800 integrated in, implemented in or communicatively coupled to said processor 910 or a kV unit 1020. The processor 910 is according to embodiments configured to receive an image 810 transmitted from said first or second receiver 22, 24 and to generate a control signal in response to the completion of transmission of an image from said first or second receiver 22, 24. The synchronizing unit 800 is in turn configured to receive a control signal from said processor 900, the control signal indicating that an image 810 has been completely transmitted from said first or second receiver 22, 24, and to synchronize the execution of tasks of the transmitters 21, 23 and/or receivers 22, 24.

In embodiments, in order to enable to synchronization the execution of tasks in the transmitters 21, 23 and/or receivers 22, 24, the synchronization unit 800 is configured to generate a synchronization signal 820 in response to the received control signal from the processor 910; and control the timing of generating and emitting an X-ray radiation pulse in said transmitters 21, 23 and/or control the timing of capturing an image receivers 22, 24 of said first and second X-ray systems 19, 20, based on said synchronization signal 820.

In embodiments, the first and second transmitters 21, 23 are configured to interpret the synchronization signal 820, and to adjust the timing of generating and emitting an X-ray radiation pulse in response to information comprised in said synchronization signal 820.

In embodiments, the first and second receivers 22, 24 are configured to interpret the synchronization signal 820 and adjust the timing of capturing an image in response to information comprised in said synchronization signal 820.

In an embodiment, the mobile control unit 2a is provided with a base module 106, a pulpit stand module 108 and an operator control interface 3b, 116.

In one or more embodiments the processor/processing unit 910 may be a processor such as a general or specific purpose processor/processing unit for example a microprocessor, microcontroller or other control logic that comprises sections of code or code portions, stored on a computer readable storage medium, such as a memory 930, that are fixed to perform certain tasks but also other alterable sections of code, stored on a computer readable storage medium, that can be altered during use. Such alterable sections of code can comprise parameters that are to be used as input for the various tasks, such as receiving user indications.

In one or more embodiments the control unit further comprises a display configured to receive a display signal from a processor 910 and to display the received signal as a displayed image, e.g. to a user control.

In one or more embodiments the control unit 2a further comprises an input device, e.g. integrated in the touch screen, configured to receive input or indications from a user as user input data.

In one or more embodiments, wherein communications interface 940 may include at least one of a Local Area Network (LAN), Metropolitan Area Network (MAN), Global System for Mobile Network (GSM), Enhanced Data GSM Environment (EDGE), High Speed Downlink Packet Access (HSDPA), Wideband Code Division Multiple Access (W-CDMA), Code Division Multiple Access (CDMA), Time Division Multiple Access (TDMA), Bluetooth®, Zigbee®, Wi-Fi, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX), infrared communications and ultrasonic communication, etc., but is not limited thereto.

In one or more embodiments, the processor/processing unit 910 is communicatively coupled and communicates with a memory 930 where data and parameters are kept ready for use by the processing unit 910. The one or more memories 930 may comprise a selection of a hard RAM, disk drive, a floppy disk drive, a magnetic tape drive, an optical disk drive, a CD or DVD drive (R or RW), or other removable or fixed media drive.

In one or more embodiments, wherein communications interface 1040 may include at least one of a Local Area Network (LAN), Metropolitan Area Network (MAN), Global System for Mobile Network (GSM), Enhanced Data GSM Environment (EDGE), High Speed Downlink Packet Access (HSDPA), Wideband Code Division Multiple Access (W-CDMA), Code Division Multiple Access (CDMA), Time Division Multiple Access (TDMA), Bluetooth®, Zigbee®, Wi-Fi, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX), infrared communications and ultrasonic communication, etc., but is not limited thereto.

In one or more embodiments, the processor/processing unit is communicatively coupled and communicates with a memory where data and parameters are kept ready for use by the processing unit. The one or more memories may comprise a selection of a hard RAM, disk drive, a floppy disk drive, a magnetic tape drive, an optical disk drive, a CD or DVD drive (R or RW), or other removable or fixed media drive.

Embodiments and Features of the Invention

Figure 5:
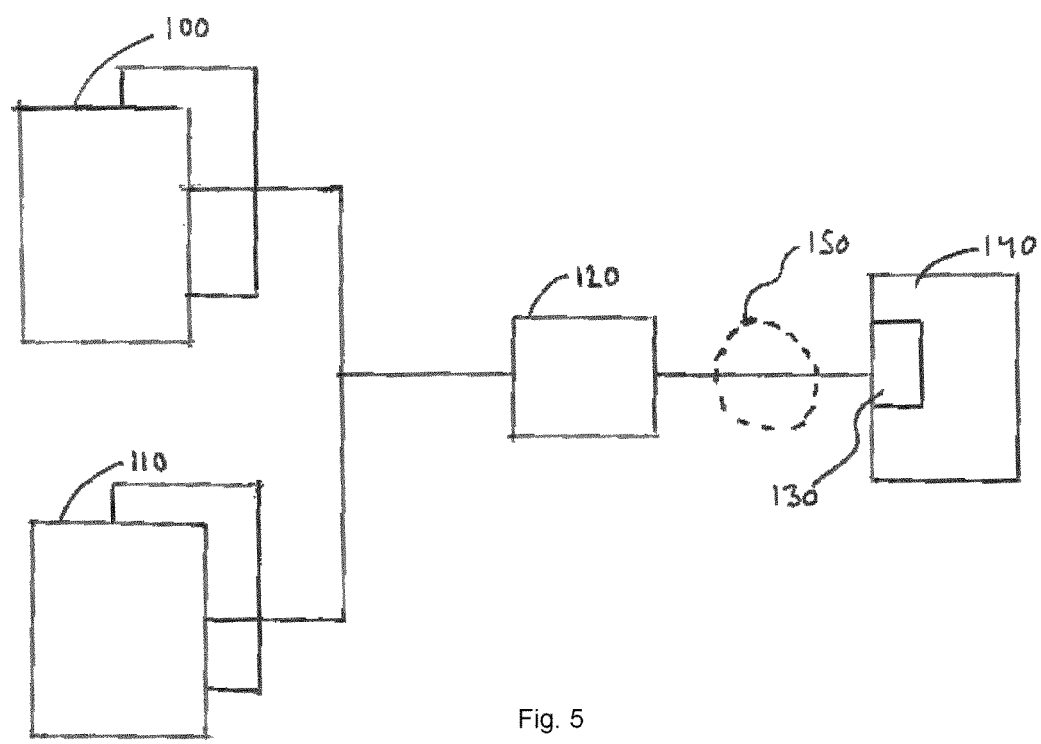
FIG. 5 shows a block diagram of a twin image detection system.

FIG. 5 shows a schematic block diagram of an architecture for synchronizing a fluoroscopy system with two x-ray systems each having a transmitter and a receiver. Said x-ray systems being attached to a mobile X-ray system carrier unit 1, wherein said x-ray systems are connected to control unit 140 through at least one cable 150.

In one embodiment said control unit 140 comprising an graphical user interface (GUI), In an alternative embodiment, the control unit may be implemented by a computing device such as a PC that may encompass the functions of said control unit 140 specially adapted for performing the steps of methods of the present disclosure, or encompass a general processor/processing unit 910 according to the description herein.

In one embodiment Control unit 140 system further comprises at least one display, that can be rotated around its foot axis, and displays scan images, e.g. to operator of the control unit, G-arm and the persons operating on the patient wherein scan images is zero or more x-ray images generated by the x-ray system. Said control unit 140 further comprises a control interface, e.g. a touch screen, keyboard, mouse or other devices with ability to interact with a user.

In one embodiment said control unit 140 comprises and is connected to an image acquisition and display system card 130. Said image acquisition and display system card 130 is connected to adaption unit 120 comprising panel video interface and decoder and configured to receive/send and decode/encode video, Ethernet-interface adapted to communicate data via an Ethernet network and panel control interface configured to receive user input. Said adaption unit 120 is connected to said x-ray systems comprising flat detectors 100 and image intensifiers 110.

Said image intensifiers 110 are configured to convert x-ray radiation into information e.g. displaying visible x-ray image of the scanned area. Furthermore image intensifiers can comprise a camera that converts data into pixel values.

Figure 6:
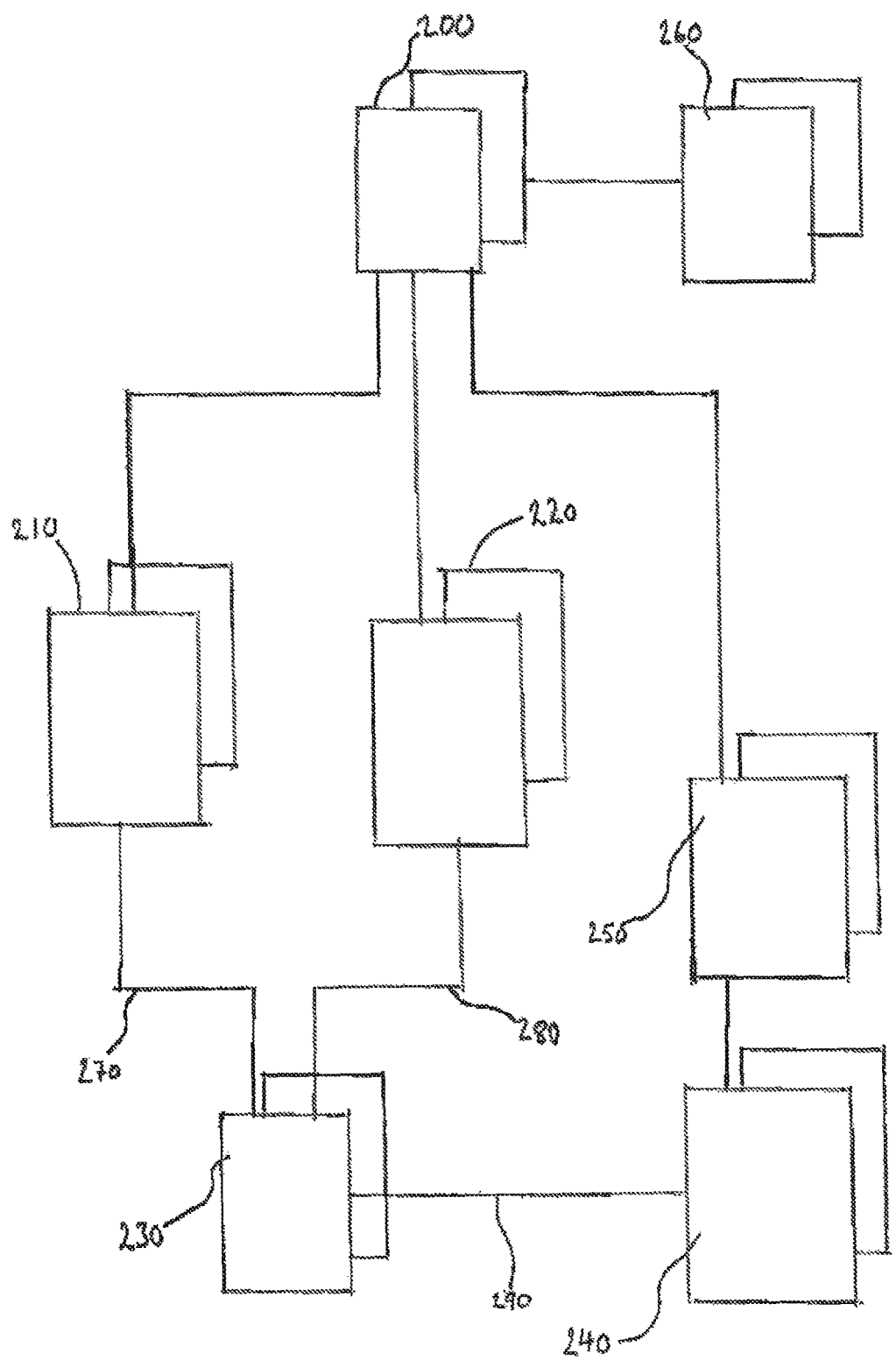
FIG. 6 shows a block diagram of a generator control.

FIG. 6 shows a schematic view of an embodiment of a system architecture of the invention. Said architecture comprises a mobile control unit connected to an input and output interface (I/O control interface) 260 wherein said interface 260 is operated whenever I/O is used in the mobile control unit 200.

Furthermore mobile control unit 200 receives a user input indicative of a control voltage value at said control display unit and sends said control voltage value to kV unit 250. Said mobile control unit 200 is further connected to a rotor unit 220, in the transmitter for the x-ray system, for x-ray tube rotation and also connected to monoblock 230.

Said monoblock 230 measures voltage used in the system and sends a measured voltage value 291 to kV unit 250 wherein kV unit 250 calculates a regulated voltage value based on said measured voltage value 291 and sends said regulated voltage value to inverter 240 wherein inverter 240 generates voltage value 290 to monoblock 230 based on and corresponding to said regulated voltage value received from kV unit 250.

Monoblock 230 sends a voltage value 280 that can be calculated to ampere by methods of milliampere (mA) sensing methods 270 to mA unit 210. Said mA unit 210 sends mA value to said mobile control unit 200.

Figure 9:
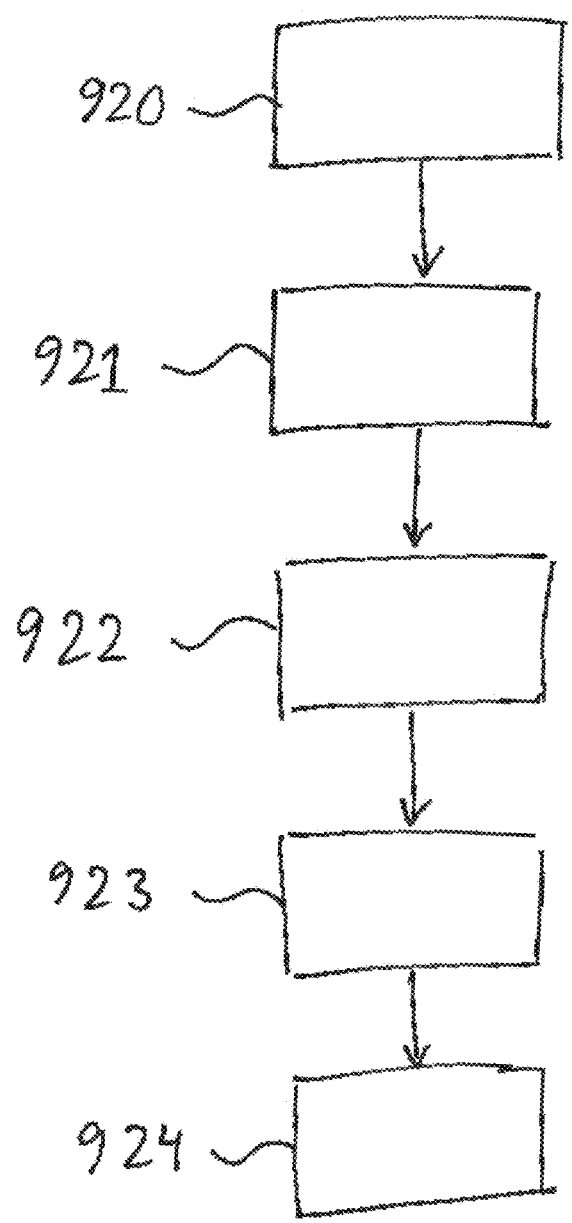
FIG. 9 shows a synchronization method according to embodiments of the invention.

According to an aspect of the invention, illustrated in FIG. 9, there is provided a method for synchronizing the signal communication in a mobile digital fluoroscopy system, the system having a mobile X-ray system carrier unit 1 comprising a first and a second X-ray device 19, 20 each having a transmitter 21, 23 and a receiver 22, 24, said respective first and second X-ray devices 19, 20 being mounted on a G-arm 18 to enable X-ray imaging in mutually intersecting planes; and a mobile control unit 2a being communicatively coupled to the mobile X-ray system carrier 1; the method comprising:

In Step S920: receiving, in a processor 910 comprised in said mobile control unit 2a, an image 810 transmitted from the first or second receiver 22, 24;

In step S921: generating in said processor 910 a control signal in response to the completion of transmission of an image 810 from said first or second receiver 22, 24; and In step S922: receiving said control signal in a synchronizing unit 800 integrated in, implemented in or communicatively coupled to said processor 910;

In step S923: generating, in said synchronizing unit 800, a synchronization signal 820 in response to said communicated control signal; and In step S924: controlling said transmitters 21, 23 and/or receivers 22, 24 of said first and second X-ray systems 19, 20.

One problem with conventional X-ray system carrier units is that limited space is available within the G-arm for a surgeon to operate. This is mainly due to bulky design of transmitters/receivers and that the height of the G-arm is limited by standard door height, as a mobile X-ray system carrier may be moved from room to room. Another problem with conventional systems is that the heavy high power transmitter parts make the X-ray system carrier units heavy to maneuver in terms of ergonomics. However, the distribution of functionality is no trivial task as all systems are closely interrelated and need to maintain synchronization, e.g. to minimize inter transmitter inter-plane interference and data overflow when transferring data, such as X-ray images, between modules in the system, such as the X-ray system carrier unit and the mobile control unit 2a.

The present invention solves this by distributing functionality between the X-ray system carrier unit and the mobile control unit 2a, synchronize transfer of image data and capturing of new image data, synchronize image capturing in different planes and by discarding images mainly reflecting scattered X-ray energy.

Due to this solution, additional space is available within the G-arm at the same time that ergonomics of moving the X-ray system carrier unit is improved, inter transmitter inter-plane interference is reduced and bandwidth requirements between the X-ray system carrier unit and the mobile control unit 2a is reduced.

Figure 14:
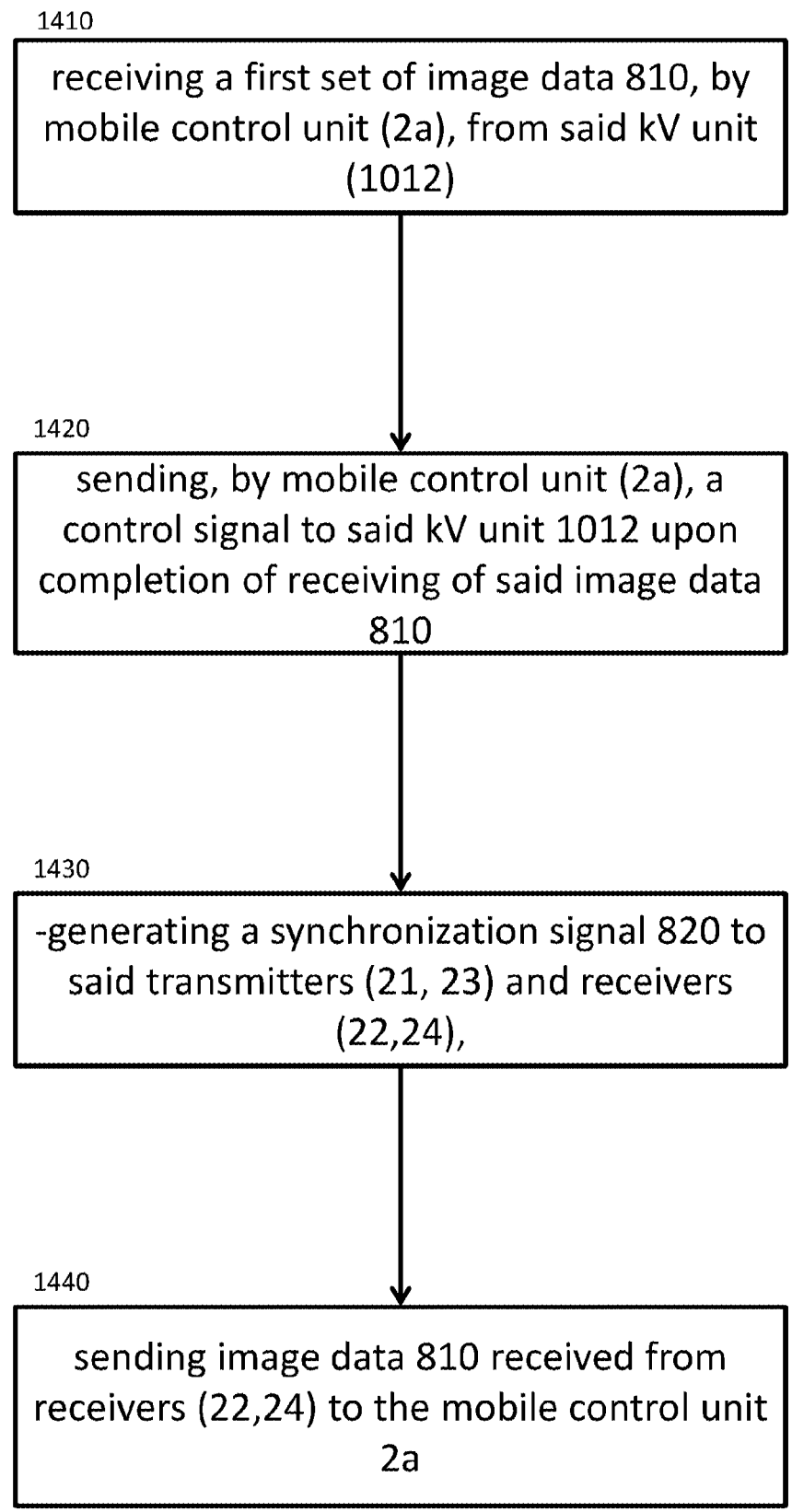

According to yet an aspect of the invention, a mobile digital fluoroscopy system comprising:
a mobile X-ray system carrier unit 1 comprising;
a first and a second X-ray device 19, 20 each having a transmitter 21, 23 and a receiver 22, 24, wherein said respective first and second X-ray devices 19, 20 being mounted on a G-arm 18 to enable X-ray imaging in mutually intersecting planes,
a kV unit 1012; and;
wherein said a mobile control unit 2a is communicatively coupled to the mobile X-ray system carrier 1 via a cable 150, wherein said mobile control unit 2a is configured to receive a first set of image data 810 from said kV unit 1012 and sending a control signal to said kV unit 1012 upon completion of receiving of said image data 810, wherein kV unit 1012 is configured to generate a synchronization signal 820 to said transmitters 21, 23 and receivers 22, 24 and to send a second set of image data 810 received from receivers 22, 24 to the mobile control unit 2a, wherein the synchronization signal 820 is configured to control timing of the first and/or second transmitter to emit/not to emit X-ray energy based on said synchronization signal 820 and to control timing of said first receiver 22 and said second receiver 24 to capture and send a second set of image data to said kV unit 1012;

In embodiments, wherein said system:
said kV unit 1012 is further configured to receive image data from first receiver 22 and said second receiver 24;
discarding image data received from said second receiver and only sending image data received from the first receiver 22 to said mobile control unit 2a; or;
discarding image data received from said first receiver and only sending image data received from the second receiver 22 to said mobile control unit 2a;
wherein discarding is based on predefined data parameters, indicative of at least an image discard pattern, retrieved from a memory 1032 communicatively coupled to said kV unit and/or functional status data in the form of user input data received from said control unit 2a;

FIG. 14 shows an embodiment of a method in fluoroscopy system for synchronizing of emitting X-ray radiation pulses, of capturing images receivers and of transferring image data from the X-ray system carrier unit 1 to the mobile control unit 2a.

According to yet an aspect of the invention, a method in a mobile digital fluoroscopy system comprising:
a mobile X-ray system carrier unit 1 comprising;
a first and a second X-ray device 19, 20 each having a transmitter 21, 23 and a receiver 22, 24, wherein said respective first and second X-ray devices 19, 20 being mounted on a G-arm 18 to enable X-ray imaging in mutually intersecting planes,
a kV unit 1012; and;
wherein said a mobile control unit 2a is communicatively coupled to the mobile X-ray system carrier 1 via a cable 150, the method comprise:
STEP 1410—receiving a first set of image data 810, by mobile control unit 2a, from said kV unit 1012,
STEP 1420—sending, by mobile control unit 2a, a control signal to said kV unit 1012 upon completion of receiving of said image data 810,
STEP 1430—generating a synchronization signal 820 to said transmitters 21, 23 and receivers 22, 24, wherein the synchronization signal 820 is configured to control timing of the first and/or second transmitter to emit/not to emit X-ray energy based on said synchronization signal 820 and to control timing of said first receiver 22 and said second receiver 24 to capture and send a second set of image data to said kV unit 1012;

STEP 1440—sending image data 810 received from receivers 22, 24 to the mobile control unit 2a;

In embodiments, the method further comprising:
receiving, by said kV unit 1012, image data from first receiver 22 and said second receiver 24;
  discarding image data received from said second receiver and only sending image data received from the first receiver 22 to said mobile control unit 2a; or;
discarding image data received from said first receiver and only sending image data received from the second receiver 22 to said mobile control unit 2a;
wherein discarding is based on predefined data parameters, indicative of at least an image discard pattern, retrieved from a memory 1032 communicatively coupled to said kV unit and/or functional status data in the form of user input data received from said control unit 2a;

According to yet an aspect of the invention, there is provided a method for synchronizing the 21, 23 X-ray emission and X-ray image retrieval in a digital fluoroscopy system, the system having a mobile X-ray system carrier unit 1 comprising a first and a second X-ray device 19, 20 each having a transmitter 21, 23 and a receiver 22, 24, and a kV unit 1012, said respective first and second X-ray devices 19, 20 being mounted on a G-arm 18 to enable X-ray imaging in mutually intersecting planes; and a mobile control unit 2a being communicatively coupled to the mobile X-ray system carrier 1 via a cable 150; the method comprising:

In Step S920: receiving, by a mobile control unit 2a, image data 810 sent from the kV unit 1012;

In step S921: upon completion of receiving of said image data 810, sending a control signal to a synchronizing unit 800 integrated in, implemented in or communicatively coupled to said kV unit 1012;

In step S923: upon reception of said control signal, generating, in said synchronizing unit 800, a synchronization signal 820, wherein said synchronization signal 820 comprises timing of generating and emitting an X-ray radiation pulse in said transmitters 21, 23 and timing of capturing an image by receivers 22, 24;

In step S924: sending said synchronization signal 820, by said kV unit 1012, to a $1^{st}$ transmitter generator 212, a $2^{nd}$ transmitter generator 232, a $1^{st}$ receiver 22 or a $2^{nd}$ receiver to:
  control the first and/or second transmitter to emit/not to emit X-ray energy based on said synchronization signal 820; and;
  control said first receiver 22 and said second receiver 24 to send image data to said kV unit 1012;

According to yet an aspect of the invention, there is provided a method for synchronizing the transmitter 21, 23 X-ray emission and X-ray image retrieval in a digital fluoroscopy system, the system having a mobile X-ray system carrier unit 1 comprising a first and a second X-ray device 19, 20 each having a transmitter 21, 23 and a receiver 22, 24, and a kV unit 1012, said respective first and second X-ray devices 19, 20 being mounted on a G-arm 18 to enable X-ray imaging in mutually intersecting planes; and a mobile control unit 2a being communicatively coupled to the mobile X-ray system carrier 1 via a cable 150; the method comprising:

In Step S920: receiving, in a processor 910 comprised in said mobile control unit 2a, image data 810 sent from the kV unit 1012, said image data received, by said kV unit 1012, from the first or second receiver 22, 24;

In step S921: generating in said processor 910 a control signal in response to detection of the completion of transmission of said image data 810 from said kV unit 1012 and sending, by said processor 910, said control signal to said kV unit 1012; and In step S922: receiving said control signal in a synchronizing unit 800 integrated in, implemented in or communicatively coupled to said kV unit 1012;

In step S923: generating, in said synchronizing unit 800, a synchronization signal 820 in response to said communicated control signal; and In step S924: sending said synchronization signal 820, by said kV unit 1012, to a $1^{st}$ transmitter generator 212, a $2^{nd}$ transmitter generator 232, a $1^{st}$ receiver 22 or a $2^{nd}$ receiver to:
  control the first and/or second transmitter to emit/not to emit X-ray energy based on said synchronization signal 820; and;
  control said first receiver 22 and said second receiver 24 to send image data to said kV unit 1012;

In embodiments, the method further comprises:
  receive image data from first receiver 22 and said second receiver 24 by said to said kV unit 1012;
  discarding image data received from said second receiver and sending image data received from the first receiver 22 to said processor 910 via a communications link 1505 in said cable 150; or; discarding image data received from said first receiver and sending image data received from the second receiver 22 to said processor 910 via a communications link 1505 in said cable 150 based on predefined data parameters, indicative of at least an image discard pattern, retrieved from a memory 1032 communicatively coupled to said kV unit and/or functional status data in the form of user input data received from said control unit 2a;

In an embodiment of step S924, controlling said transmitters 21, 23 and/or receivers 22, 24 of said first and second X-ray systems 19, 20 comprises communicating said synchronization signal 820 to said transmitters 21, 23 and adjusting the timing of emitting an X-ray radiation pulse in response to information comprised in said synchronization signal (820).

In an embodiment of step S924, controlling said transmitters 21, 23 and/or receivers 22, 24 comprises communicating said synchronization signal 820 to said receivers 22, 24 and adjusting the timing of capturing an image in response to information comprised in said synchronization signal 820.

In an embodiment of step S924, controlling said transmitters 21, 23 and/or receivers 22, 24 comprises controlling the timing of emitting an X-ray radiation pulse in said transmitters 21, 23 and controlling the timing of capturing an image receivers 22, 24 of said first and second X-ray systems 19, 20, based on said synchronization signal 820.

Figure 7:
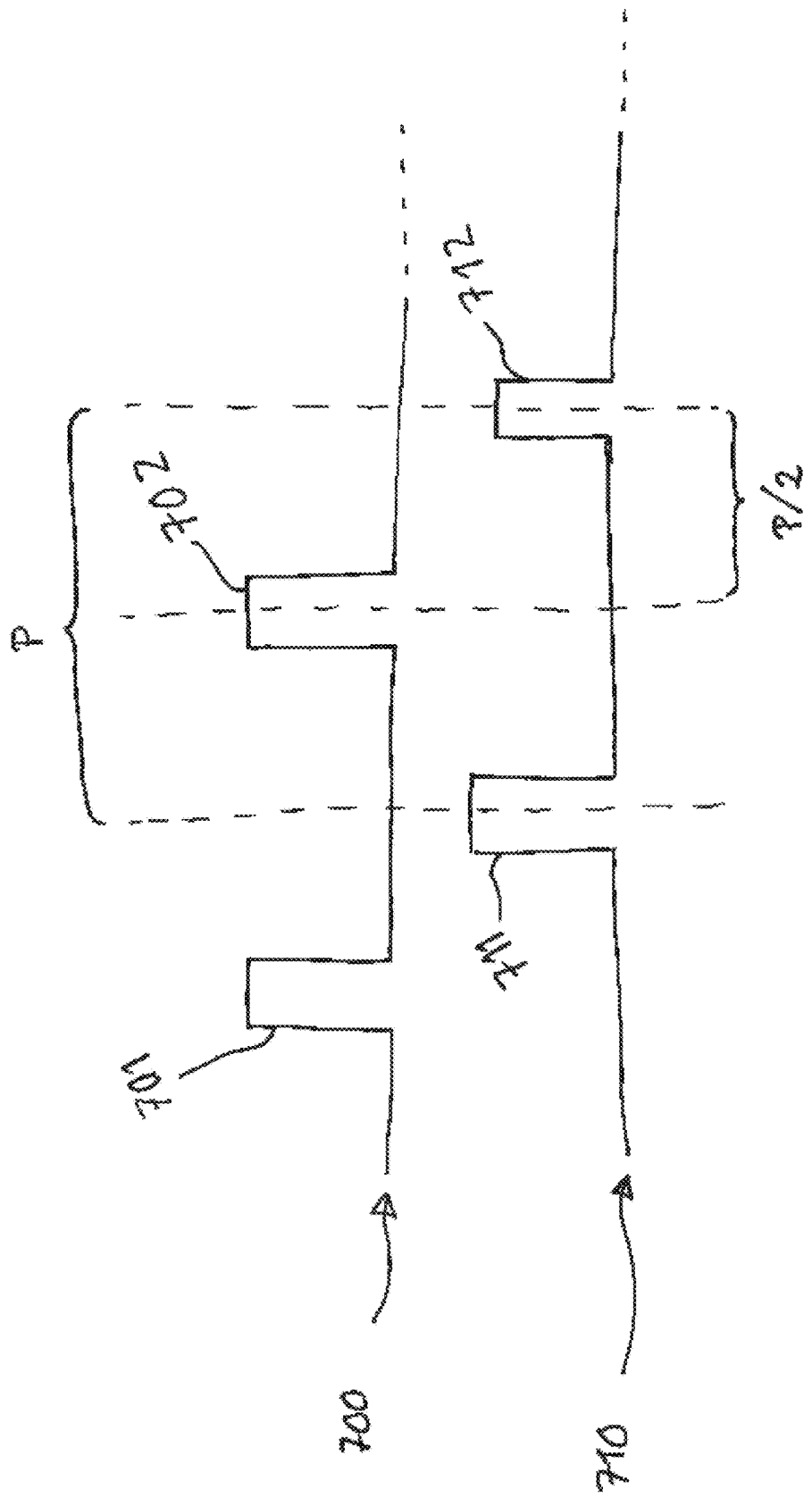
FIG. 7 shows a schematic view of embodiments of signal synchronization.

In FIG. 7 a schematic view of embodiments of signal synchronization is shown. In FIG. 7, there are two image transmission sequences 700 and 710, with images captured by and transmitted from the first and second receiver 22, 24, respectively. As can be seen from the figure, images 701, 702 et cetera are transmitted from the first receiver 22, to the mobile control unit 2a, at a frame rate P. Images 703, 704 et cetera are transmitted from the second receiver 22, to the mobile control unit 2a, at a frame rate P, but with a delay of P/2 compared to the frames being transmitted from the first receiver 22.

As described above, when an image 701 has been fully received (complete transmission) by the processor 910 of the mobile control unit 2a, the processor 910 communicates this to the synchronization unit 800, using a control signal, thereby triggering the synchronization unit 800 to generate a synchronization signal 820. If the latest received image frame, e.g. 701, was captured by and transmitted from the first receiver 22, the synchronization signal is communicated to the second transmitter 23, thereby triggering the second transmitter 23 to generate and emit an X-ray pulse; and to the second receiver 24 thereby triggering the second receiver 23 to capture and an image 702 and to transmit the image to the mobile control unit 2a. On the other hand, if the latest received image frame was captured by and transmitted from the second receiver 24, e.g. image 702, the synchronization signal is communicated to the first transmitter 21, thereby triggering the first transmitter 21 to generate and emit an X-ray pulse; and to the first receiver 22 thereby triggering the first receiver 22 to capture and an image 703 and to transmit the image to the mobile control unit 2a. Thereby, the emission of X-rays, image capturing and transmission of images is alternated between the first and the second X-ray devices 19, 20.

Through this alternating mode, achieved through synchronization of the X-ray devices 19, 20 based on the rate of capturing and transmission of images to the mobile control unit 2a, the problem of having noisy images is solved. As no X-ray pulse is generated and no image is captured until the previously captured image has been completely transmitted to, or read out at, the mobile control unit 2a, there will be no interference between X-ray radiation emitted along the first plane and X-ray radiation emitted along the second plane. Thereby, higher quality images, with reduced amount of noise, are obtained. The images are also easier for an observer to interpret, as noise that may have drawn attention to non-important image information, or hidden important image information, is removed.

Another advantageous effect obtained is the fact that the alternating image signals transmitted from the first and the second receivers 22, 24 may be transmitted using a single cable or channel, without introduction of delay, as the receivers 22, 24 will send the images alternatingly. Thereby, the problems with the conventional systems, that the system requires a large amount of cables, thereby increasing cost and complexity of the system, decreasing the mobility of the system and increasing the risk of personnel involved tripping or disconnecting a cord during operation of the system, is reduced.

In one embodiment, scan images can be stored within the system and presented as last image hold or a set of scan images stored in a flow as a last sequence hold. This furthers perception of scanned parts as well as progress and current status of operation. One use case scenario can be to monitor the effects and progress of operation on the patient by having the option to see scan image before a small operation and thus see a full extent of last surgical operation made.

In one embodiment, control unit is outfitted with several displays. Top displays can be outfitted at top of control unit with turn able foot giving the option for surgeon to view scan images on display without moving from operation position Displays can further be outfitted at control panel on said control unit resulting in enhanced control of x-ray emitters as well as the option to view scan images while said top display is turned in other direction from user of control unit. In one embodiment, user of control unit is able to operate collimator in order to control/focus the dosage of irradiation onto the area of interest causing the patient to be exposed to a decreased dosage of radiation. Wherein control of said collimators is performed by control unit table e.g. by touch screen, keyboard and other . . . .

In one or more embodiments there is provided a computer program product comprising non-transitory computer readable code configured to, when executed in a processor, perform any or all of the method steps or functions described herein.

Use case scenarios can be the user at the control unit inputting an estimated kV value. Estimated kV value might not be a high enough value for emitted radiation to scan the patient deep enough in order to get a clear view of area of interest. Mobile control unit uses methods by calculation and regulation to calculate how much more kV the system needs in order to successfully scan the area of interest. This works as well if the kV is too high, the regulation then send a regulated kV value for the system to compensate for. The regulated kV value can be zero as well. This is especially good for the one operating the control unit as the user can view a displayed value at the control unit as well the last image scanned and the system displaying the regulation needed. This unnecessary time to calibrate kV in order to scan the area of interest is thus eliminated.

One problem when operating an X-ray system having a first and second X-ray device is that the receiver 24 configured to receive an X-ray beam along the second plane P2 will register radiation emitted by the first transmitter 21, aligned along the plane P1, due to scattering. To reduce this inter-transmitter interference, the inventor has realized that transmission/emission by the first transmitter and the second transmitter could be separated temporally.

The present invention solves this by synchronizing transmitter activation timing and image retrieval timing from the receivers. An advantage of the current invention is that interference between X-ray radiation emitted by a first transmitter along the first plane and X-ray radiation emitted by a second emitter along the second plane is reduced. Yet another advantage is that bandwidth requirements for the connection 1505 communicatively connecting the X-ray system carrier unit and the control unit 2a, 140, 200, 1010 1010 as only one out of two captured images is transferred each time after capturing the images.

Figure 10:
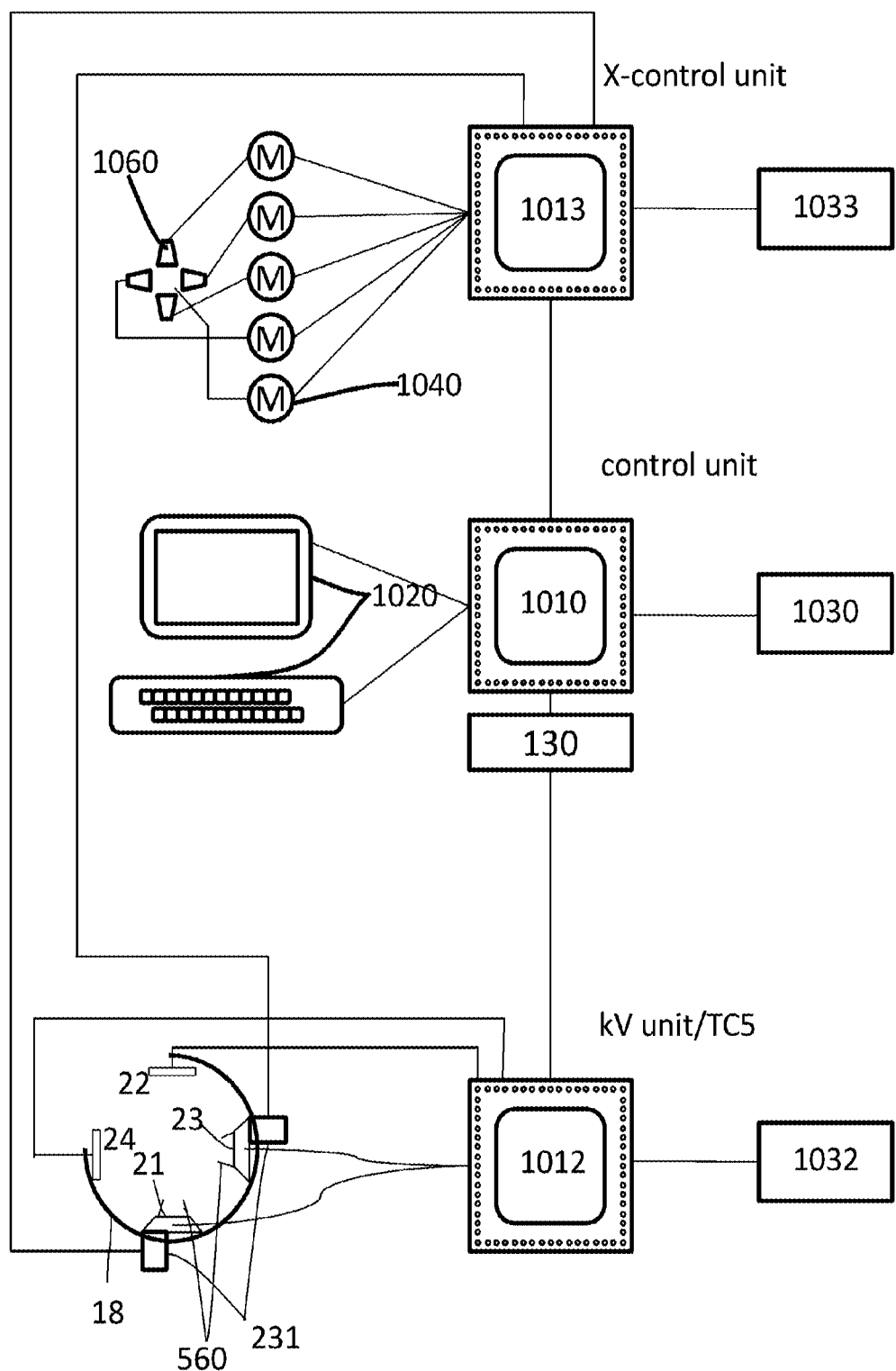
FIG. 10 shows a schematic view of an embodiment of a system of the invention.

FIG. 10 shows a schematic view of an embodiment of a system architecture of the invention, wherein the system comprises a control unit 2a, 140, 200, 1010, a kV unit 1012, and an x-control unit 1013. The X-ray beam transmitter is controlled by a kV unit 1012 comprised at the X-ray system carrier unit 1. In one embodiment, the kV unit is configured to determine the X-ray energy to be emitted by the transmitter at a particular time and to control transmitters to emit/not to emit said determined X-ray energy based on predefined data parameters retrieved from a memory 1032 communicatively coupled to said kV unit and/or functional status data in the form of user input data received from said control unit 2a, 140, 200, 1010. In one embodiment, the kV unit is further configured to send third control data indicative of X-ray beam transmission to said control unit 2a, 140, 200, 1010. In one embodiment, the kV unit 1012 further configured to read out or receive image data from the receivers 22, 24 and send image data via a network connection 1505, e.g. Ethernet, in a cable 150 to the control unit 2a, 140, 200, 1010. The kV unit 1012 further determines the X-ray beam dose administered to an object, e.g. a patient, based on image data retrieved from the receivers, e.g. by determining an image quality measure/value based on the image intensity, as would be understood by a skilled person. In one embodiment the kV unit 1012 is further configured to calculate a regulated voltage value by determining an image quality value based on image intensity an perform a look-up operation in a predefined look-up table based on said image quality value 291 to obtain a regulated voltage value. In one embodiment, the kV unit is further configured to send functional status data indicative of the determined X-ray beam dose to said control unit 2a, 140, 200, 1010 and to determine the X-ray beam dose administered to an object, e.g. a patient. The kV unit 1012, the transmitters 21, 23, the receivers 22, 24, the memory 1032 and the control unit 2a, 140, 200, 1010 are communicatively coupled to each other, for instance by means of a cable or through wireless signal transmission. The area of interest or area radiated by the X-ray beam may be controlled by narrowing the X-ray beam by the use of collimator plates 1060 disposed between a beam transmitter and a beam receiver. The control of the area of interest is achieved by the use of a x-control unit 1013 configured or adapted to receive functional status data as control data in the form of control signals from said control unit 2a, 140, 200, 1010, wherein the control data is based on processed user input data, to control servo motors 1040 to a predetermined position based on said control data by sending servo motor signals, thereby narrowing the area of interest of the patient exposed to the X-ray beam. In one embodiment, the x-control unit 1013 is further configured to obtain dose area product (DAP) measurement values from a DAP chamber 231, also referred to as ionization chamber. Dose area product (DAP) is a quantity used in assessing the radiation risk from diagnostic x-ray examinations and interventional procedures. It is defined as the absorbed dose multiplied by the area irradiated, typically expressed in gray square centimeters ($Gy*cm^2$), $mGy*cm^2$ or $cGy*cm^2$. Examples of DAP measurement values are cumulative dose, DAP dose and entrance dose. Functional status data indicative of the status of a servo motor is obtained by the x-control unit by receiving servo motor signals and to send functional status data as status control signals to said control unit 2a, 140, 200, 1010. In one embodiment the x-control unit is configured to receive functional status data as control signals from said control unit 2a, 140, 200, 1010, wherein the control data is based on processed user input data, to control servo motors to a predetermined position based on said functional status data by sending servo motor signals, thereby narrowing the area of interest of the patient exposed to the X-ray beam and to obtain functional status data indicative of the status of a servo motor by receiving servo motor signals and to send functional status data as status control signals to said first control unit 2a, 140, 200, 1010. The x-control unit 1013, the DAP chambers 231, the control unit 2a, 140, 200, 1010 and the servo motors are communicatively coupled to each other, for instance by means of a cable or through wireless signal transmission.

Figure 11:
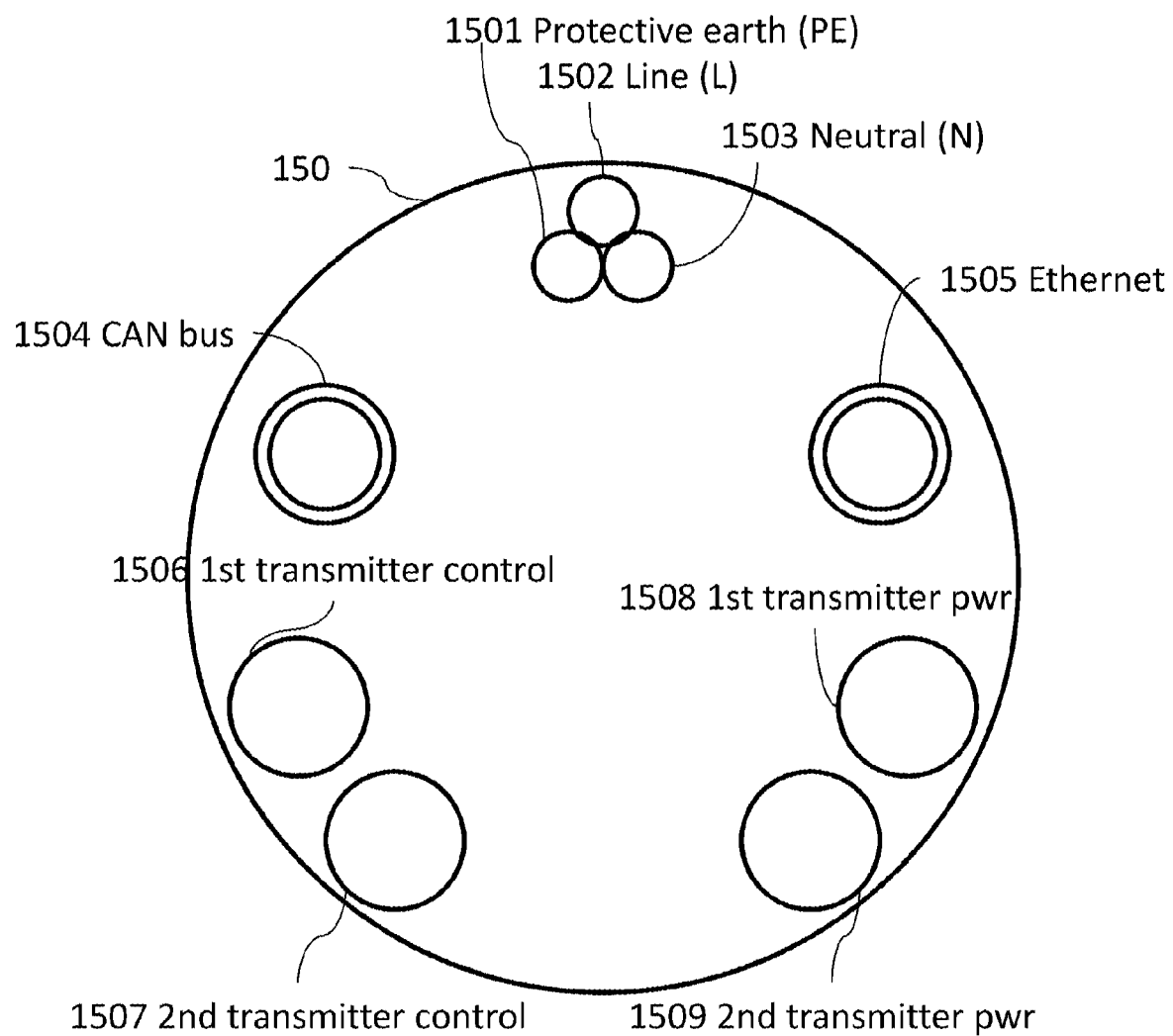
FIG. 11 shows a schematic view of an embodiment of a cable connecting the X-ray system carrier unit with the control unit.

FIG. 11 shows a schematic view of an embodiment of a cable 150 connecting the X-ray system carrier unit 1 with the control unit 2a, 140, 200, 1010. The cable 150 comprise mains-connections 1501 protective earth (PE), 1502 line (L) and 1503 neutral (N), 1504 CAN bus, 1505 Ethernet, 1506 $1^{st}$ transmitter control, 1507 $2^{nd}$ transmitter control, 1508 $1^{st}$ transmitter high power supply and 1509 $2^{nd}$ transmitter high power supply. The mains-connections 1501 protective earth (PE), 1502 line (L) and 1503 neutral (N) provides main power supply from X-ray system carrier unit 1 to the control unit 2a, 140, 200, 1010 or vice versa. The 1504 CAN bus connects the x-control unit 1013 to the control unit 2a, 140, 200, 1010 directly or via the display system card 130 and transfers functional status data in both directions, e.g. indicative of a predetermined position to control servo motors 1040 to or DAP parameter values. The 1505 connects the kV unit/TC5 unit to the control unit 2a, 140, 200, 1010 directly or via the display system card 130 and transfers functional status data in both directions, e.g. indicative of captured X-ray images, target power of the transmitters (21,23) in kV or mA values and activation timing of the transmitters. The 1506 $1^{st}$ transmitter control connects the first transmitter to a transmitter generator unit and transfers functional status data in both directions, e.g. indicative of detected errors. The 1507 $2^{nd}$ transmitter control connects the second transmitter to a transmitter generator unit and transfers functional status data in both directions, e.g. indicative of detected errors. The 1508 $1^{st}$ transmitter high power supply connects the first transmitter 21 to a first inverter unit and transfers high power to the first transmitter 21 or monoblock. The 1509 $2^{nd}$ transmitter high power supply connects the second transmitter 23 to a second inverter unit and transfers high power to the second transmitter 23 or monoblock.

Figure 12:
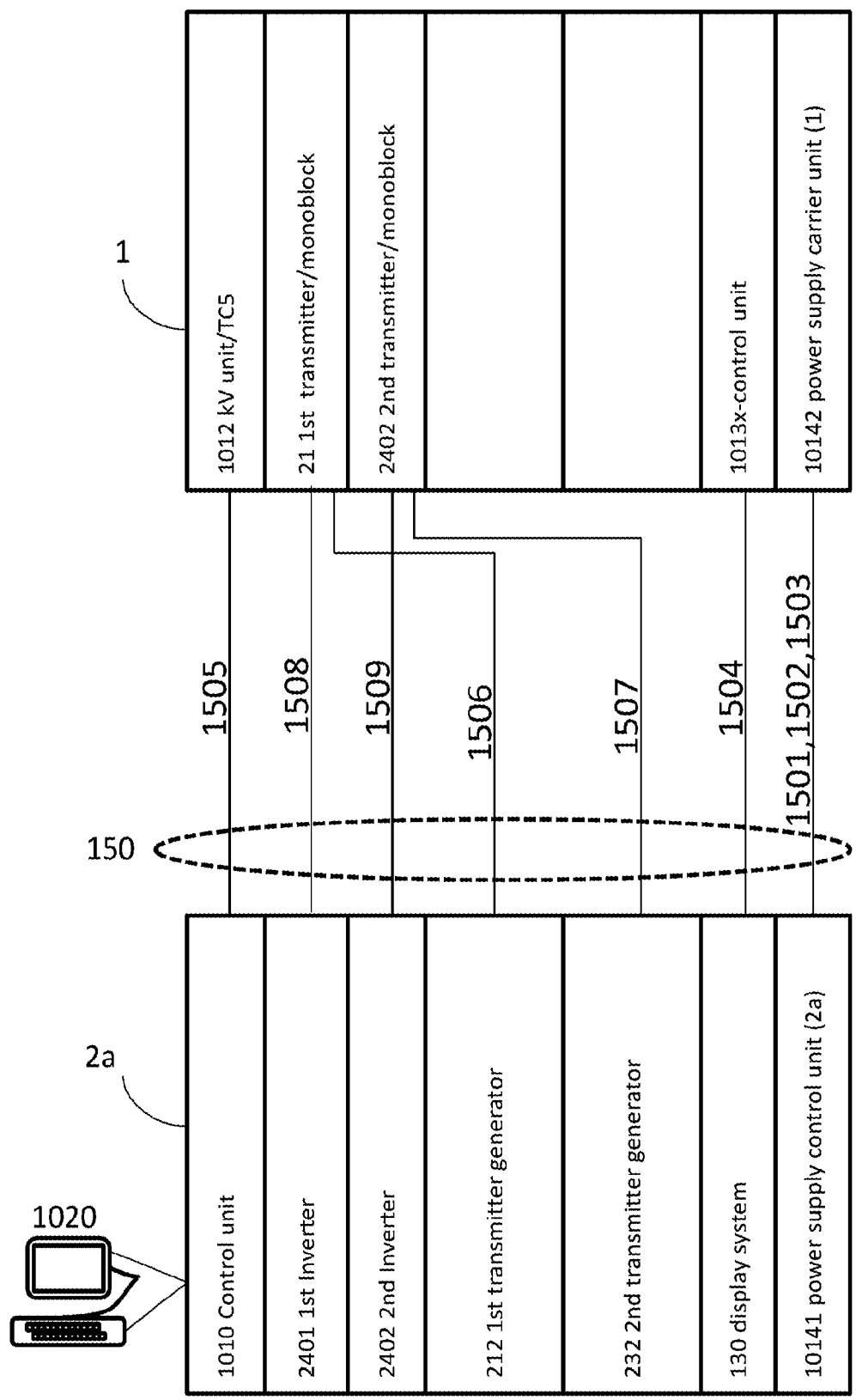
FIG. 12 shows an embodiment of a fluoroscopy system comprising a mobile X-ray system carrier communicatively coupled to a mobile control unit by a cable.

FIG. 12 shows a schematic view of an embodiment of a mobile digital fluoroscopy system, comprising: a mobile X-ray system carrier unit 1 having a first and a second X-ray device 19, 20 each having a transmitter 21, 23 and a receiver 22, 24, said respective first and second X-ray devices 19, 20 being mounted on a G-arm 18 to enable X-ray imaging in mutually intersecting planes; a mobile control unit 2a, wherein the mobile X-ray system carrier 1 is communicatively coupled to the mobile control unit 2a by a cable 150; The cable 150 comprise mains-connections 1501 protective earth (PE), 1502 line (L) and 1503 neutral (N), 1504 CAN bus, 1505 Ethernet, 1506 $1^{st}$ transmitter control, 1507 $2^{nd}$ transmitter control, 1508 $1^{st}$ transmitter high power supply and 1509 $2^{nd}$ transmitter high power supply. The mains-connections 1501 protective earth (PE), 1502 line (L) and 1503 neutral (N) provides power from X-ray system carrier unit power supply 10142 to the control unit power supply 10141 or vice versa. The 1504 CAN bus connects the x-control unit 1013 to the control unit 2a, 140, 200, 1010 directly (not shown in image) or via the display system card 130 and transfers functional status data in both directions, e.g. indicative of a predetermined position to control servo motors 1040 to or DAP parameter values. The 1505 connects the kV unit/TC5 unit 1012 to the control unit 2a, 140, 200, 1010 directly or via the display system card 130 (not shown in the image) and transfers functional status data in both directions, e.g. indicative of captured X-ray images, target power of the transmitters 21, 23 in kV or mA values and activation timing of the transmitters. The 1506 $1^{st}$ transmitter control connects the first transmitter 21 to a transmitter generator unit 212 and transfers functional status data in both directions, e.g. indicative of detected errors in the transmitter/monoblock. The 1507 $2^{nd}$ transmitter control connects the second transmitter 23 to a transmitter generator unit 232 and transfers functional status data in both directions, e.g. indicative of detected errors. The 1508 $1^{st}$ transmitter high power supply connects the first transmitter 21 to a first inverter unit 2401 and transfers high power to the first transmitter 21 or monoblock. The 1509 $2^{nd}$ transmitter high power supply connects the second transmitter 23 to a second inverter unit 2402 and transfers high power to the second transmitter 23 or monoblock.

Figure 13A:
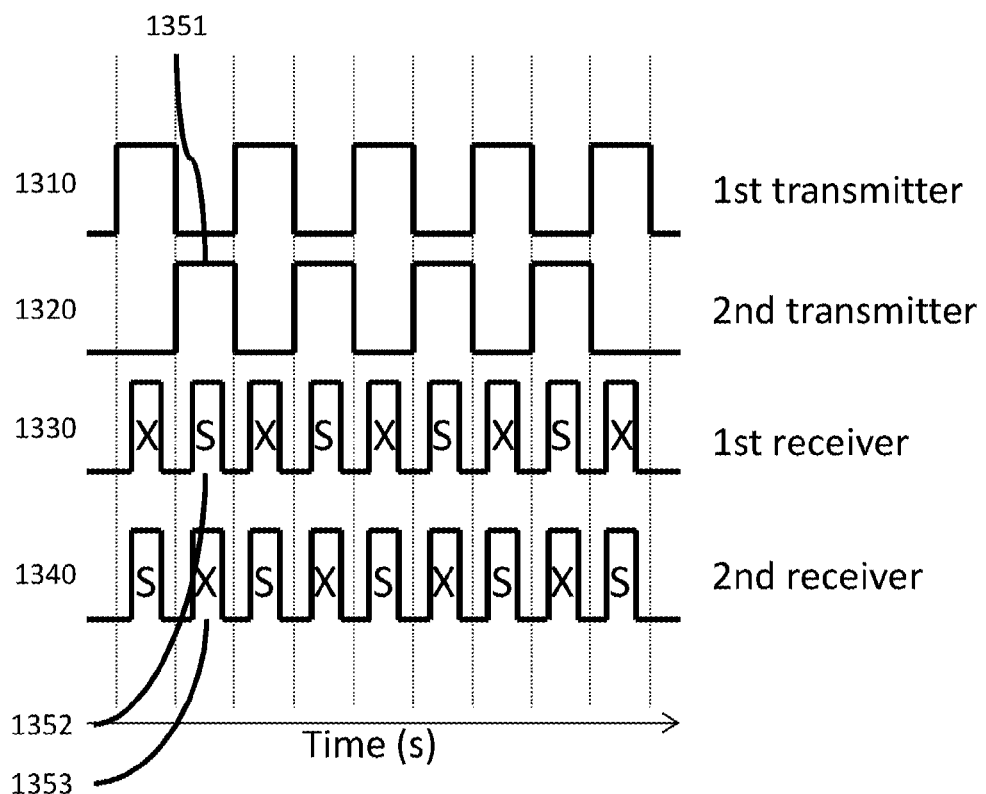
FIG. 13a shows a schematic view of synchronization signal 820 and an image discard pattern.

FIG. 13a shows a schematic view of an embodiment of a synchronization signal 820 and an image discard pattern. In one embodiment the synchronization signal 820 comprises a first signal part sent 1310 to the $1^{st}$ transmitter 21, a second signal part 1320 sent to the $2^{nd}$ transmitter 23, a third signal part 13330 sent to the $1^{st}$ receiver 22 and a fourth signal part 1340 sent to the $2^{nd}$ receiver 24, wherein said first part 1310 comprises timing of emitting an X-ray radiation pulse in said $1^{st}$ transmitter 21, wherein said second part 1320 comprises timing of emitting an X-ray radiation pulse in said $2^{nd}$ transmitter 23, wherein said third part comprises timing of capturing an image by said $1^{st}$ receiver 22, wherein said fourth part comprises timing of capturing an image by said 2nd receiver 22. A high synchronization signal 820 value, such as a signal value 1351 shown in FIG. 13a, indicates activation and a low synchronization signal 820 value indicates de-activation of transmitters 21, 23 or receivers 22, 24. In one embodiment, the image discard pattern, retrieved from a memory 1032 communicatively coupled to said kV unit, is overlaid on the synchronization signal 820 in FIG. 13a. Images denoted by "X" represents images captured by a receiver 22, 24 when the corresponding transmitter 21, 23 oriented in the same plane is emitting X-ray energy which are sent to the control unit 2a, 140, 200, 1010, e.g. when the $2^{nd}$ transmitter is active 1351, a second image 1353 comprising image data is captured by the $2^{nd}$ receiver and sent to the control unit 2a, 140, 200, 1010. Images denoted by "S" represents images captured by a receiver (22,24) when the corresponding transmitter (21,23) oriented in the same plane is not emitting X-ray energy and which are discarded, e.g. when the $2^{nd}$ transmitter is active 1351, a first image 1352 comprising image data is captured by the 1st receiver discarded by the kV unit 1012. The energy captured by the $1^{st}$ receiver in this case is mainly scattered energy from the $2^{nd}$ transmitter oriented in a different plane. The energy captured by the $2^{nd}$ receiver in this case is mainly energy from the $2^{nd}$ transmitter oriented in the same plane. In embodiments, the first signal part sent 1310 and the second signal part 1320 for the transmitter have longer active periods or pulse width than active periods for the corresponding third signal part 13330 and fourth signal part 1340 for the receivers. In embodiments, the third signal part 13330 and fourth signal part 1340 for the receivers have longer active periods or pulse width than active periods for the first signal part sent 1310 and the second signal part 1320 for the transmitter.

Figure 13B:
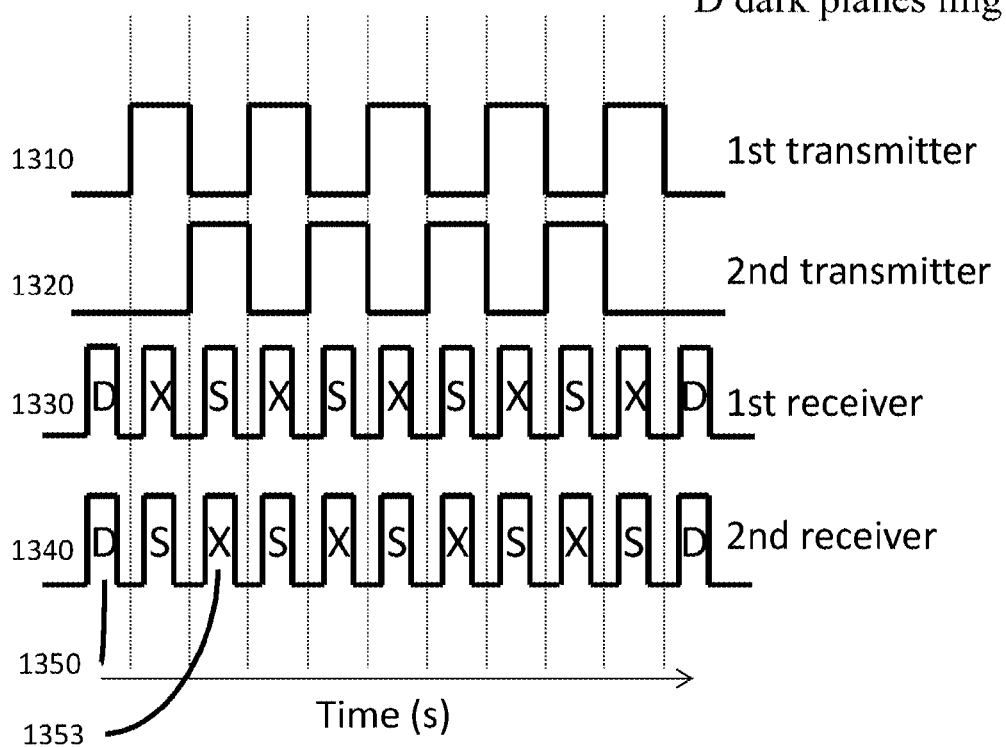
FIG. 13b shows a schematic view of an embodiment of a syschronization signal 820 and an image discard pattern.

FIG. 13b shows a schematic view of an embodiment of a synchronization signal 820 and an image discard pattern. In one embodiment the synchronization signal 820 comprises a first signal part sent 1310 to the $1^{st}$ transmitter 21, a second signal part 1320 sent to the $2^{nd}$ transmitter 23, a third signal part 13330 sent to the $1^{st}$ receiver 22 and a fourth signal part 1340 sent to the $2^{nd}$ receiver 24, wherein said first part 1310 comprises timing of emitting an X-ray radiation pulse in said $1^{st}$ transmitter 21, wherein said second part 1320 comprises timing of emitting an X-ray radiation pulse in said $2^{nd}$ transmitter 23, wherein said third part comprises timing of capturing an image by said $1^{st}$ receiver 22, wherein said fourth part comprises timing of capturing an image by said 2nd receiver 22. A high synchronization signal 820 value, such as a signal value 1351 shown in FIG. 13b, indicates activation and a low synchronization signal 820 value indicates de-activation of transmitters 21, 23 or receivers 22, 24. In one embodiment, the image discard pattern, retrieved from a memory 1032 communicatively coupled to said kV unit, is overlaid on the synchronization signal 820 in FIG. 13b, wherein the image discard pattern defines the intended use for a captured image, e.g. send to control unit 2a, 140, 200, 1010, discard image or be used as a "dark image" for removing dark current noise, i.e. noise present when none of the transmitters are transmitting or emitting X-ray energy. Images denoted by "X" represents images captured by a receiver 22, 24 when the corresponding transmitter 21, 23 oriented in the same plane is emitting X-ray energy which are sent to the control unit 2a, 140, 200, 1010, e.g. when the $2^{nd}$ transmitter is active 1351, a second image 1353 comprising image data is captured by the $2^{nd}$ receiver and sent to the control unit 2a, 140, 200, 1010. Images denoted by "S" represents images captured by a receiver 22, 24 when the corresponding transmitter 21, 23 oriented in the same plane is not emitting X-ray energy and which are discarded, e.g. when the $2^{nd}$ transmitter is active 1351, a first image 1352 comprising image data is captured by the 1st receiver discarded by the kV unit 1012. The energy captured by the $1^{st}$ receiver in this case is mainly scattered energy from the $2^{nd}$ transmitter oriented in a different plane. The energy captured by the $2^{nd}$ receiver in this case is mainly energy from the $2^{nd}$ transmitter oriented in the same plane. Images denoted by "D" represents images captured by a receiver 22, 24 when neither of the transmitters 21, 23 are emitting X-ray energy. As can be seen from the image the D images may be captured at the beginning and at the end of an image sequence and can be used directly in the kV unit 1012 or after being sent to the control unit 2a for reducing background noise or dark current noise. In one example, this is done by subtracting image data values from the D-image 1350 from data values from an X-image 1351, as would be understood by the skilled person.

Figure 15:
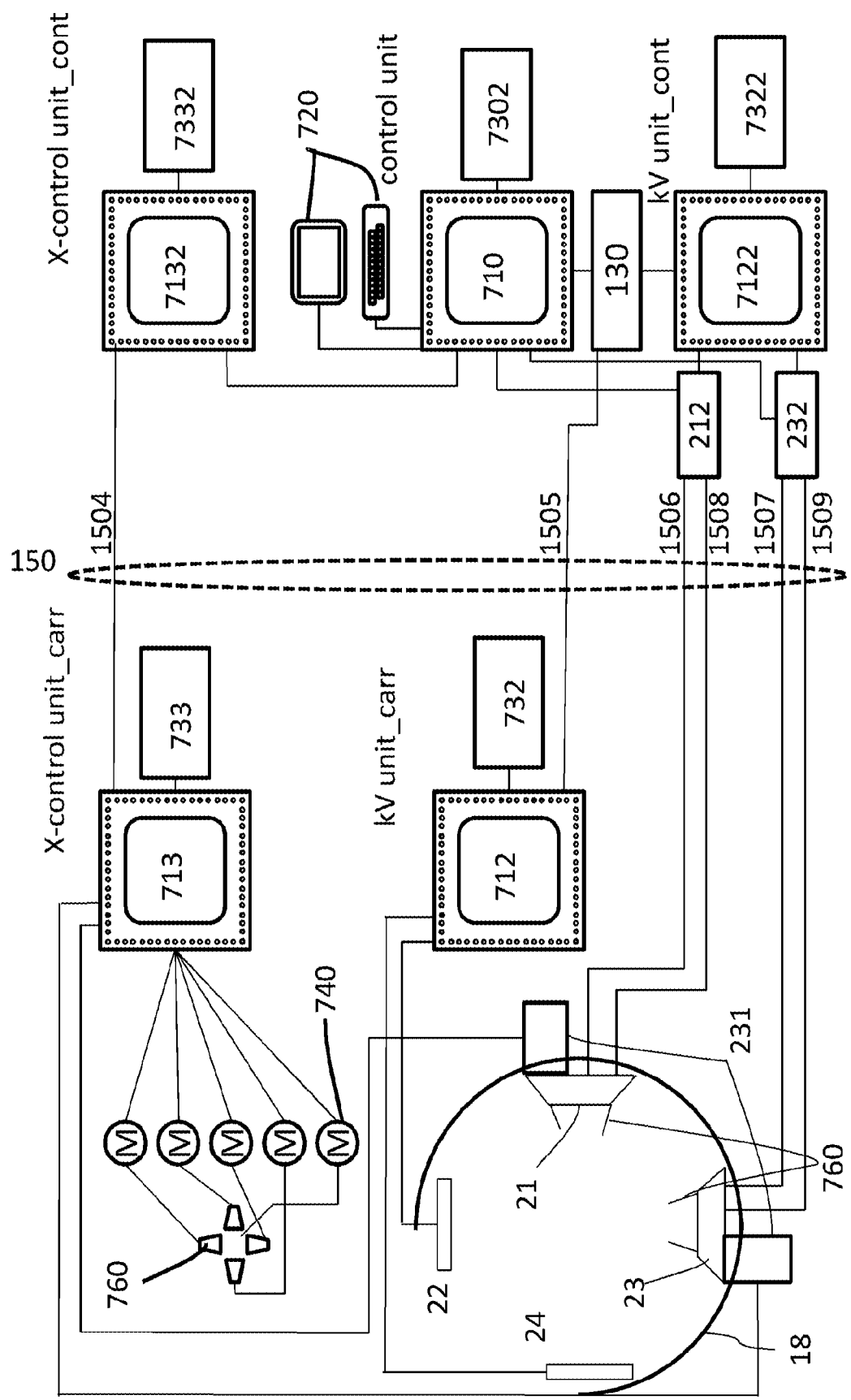
FIG. 15 shows a schematic view of yet an embodiment of a system of the invention.

FIG. 15 shows a schematic view of an embodiment of the invention, wherein the system comprises a control unit 2a, 140, 200, 710 710, a kV unit 712, a kV unit_cont 7122 communicatively coupled to a memory 7322, an x-control unit 713 and an x-control unit_cont 7132 communicatively coupled to a memory 7332. In embodiments, the kV unit 712 and the x-control unit 713 are communicatively coupled via a cable 150 to the x-control unit_cont 7132, kV unit_cont 7122 and the control unit 2a. In embodiments, the kV unit 712 is communicatively coupled via a network connection 1505, e.g. Ethernet, in the cable 150 to the kV unit_cont 7122. In embodiments, the x-control unit 713 is communicatively coupled via a connection 1505, e.g. a Controller Area Network (CAN) bus, in the cable 150 to the x-control unit_cont 7132. In embodiments, the system further comprise a $1^{st}$ transmitter generator unit 212 communicatively coupled to the kV unit_cont 7122 and the control unit 2a, 140, 200, 710 710. In embodiments, the $1^{st}$ transmitter generator unit 212 is further coupled to the $1^{st}$ transmitter by transmitter high power supply, connection 1508. In embodiments, the $1^{st}$ transmitter generator unit 212 is further coupled to the $1^{st}$ transmitter by a 1506 $1^{st}$ transmitter control. In embodiments, the system further comprise a $2^{nd}$ transmitter generator unit 232 communicatively coupled to the kV unit_cont 7122 and the control unit 2a, 140, 200, 710 710. In embodiments, the $2^{nd}$ transmitter generator unit 232 is further coupled to the $2^{nd}$ transmitter by transmitter high power supply, connection 1509 in cable 150. In embodiments, the $2^{nd}$ transmitter generator unit 232 is further coupled to the $2^{nd}$ transmitter by a 1507 $2^{nd}$ transmitter control connection in cable iso. The X-ray beam transmitters 21, 23 are controlled by a kV unit 712 comprised at the X-ray system carrier unit. In embodiments, the X-ray beam transmitters 21, 23 are further controlled via a kV unit_cont 7122 comprised at control unit 2a, 140, 200, 710. In one embodiment, the kV unit is configured to determine the X-ray energy to be emitted by the transmitter at a particular time and to control transmitters to emit/not to emit said determined X-ray energy based on predefined data parameters retrieved from a memory 732 communicatively coupled to said kV unit 712 and functional status data in the form of user input data received from said control unit 2a, 140, 200, 710. In one embodiment, the kV unit_cont 7122 is configured to determine the X-ray energy to be emitted by the transmitter at a particular time and to control transmitters to emit/not to emit said determined X-ray energy based on predefined data parameters retrieved from a memory 7322 communicatively coupled to said kV unit_cont 7122 and functional status data in the form of user input data received from said control unit 2a, 140, 200, 710. In one embodiment, the kV unit 712 is further configured to send third control data indicative of X-ray beam transmission to said control unit 2a, 140, 200, 710. In one embodiment, the kV unit 712 further configured to read out or receive image data from the receivers (22,24) and send image data via a network connection 1505, e.g. Ethernet, in a cable 150 to the control unit 2a, 140, 200, 710. The kV unit 712 further determines the X-ray beam dose administered to an object, e.g. a patient, based on image data retrieved from the receivers, e.g. by determining an image quality measure/value based on the image intensity, as would be understood by a skilled person. In one embodiment the kV unit 712 is further configured to calculate a regulated voltage value by determining an image quality value based on image intensity an perform a look-up operation in a predefined look-up table based on said image quality value 291 to obtain a regulated voltage value. In one embodiment, the kV unit is further configured to send functional status data indicative of the determined X-ray beam dose to said control unit 2a, 140, 200, 710 and to determine the X-ray beam dose administered to an object, e.g. a patient. The kV unit 712, the transmitters 21, 23, the receivers 22, 24, the memory 732 and the control unit 2a, 140, 200, 710 are communicatively coupled to each other, for instance by means of a cable or through wireless signal transmission. The area of interest or area radiated by the X-ray beam may be controlled by narrowing the X-ray beam by the use of collimator plates 760 disposed between a beam transmitter and a beam receiver. The control of the area of interest is achieved by the use of a x-control unit 713 configured or adapted to receive functional status data as control data in the form of control signals from said control unit 2a, 140, 200, 710, wherein the control data is based on processed user input data, to control servo motors 740 to a predetermined position based on said control data by sending servo motor signals, thereby narrowing the area of interest of the patient exposed to the X-ray beam. In one embodiment, the x-control unit 713 is further configured to obtain dose area product (DAP) measurement values from a DAP chamber 231, also referred to as ionization chamber. Dose area product (DAP) is a quantity used in assessing the radiation risk from diagnostic x-ray examinations and interventional procedures. It is defined as the absorbed dose multiplied by the area irradiated, typically expressed in gray square centimeters ($Gy*cm^2$), $mGy*cm^2$ or $cGy*cm^2$. Examples of DAP measurement values are cumulative dose, DAP dose and entrance dose. Functional status data indicative of the status of a servo motor is obtained by the x-control unit by receiving servo motor signals and to send functional status data as status control signals to said control unit 2a, 140, 200, 710. In one embodiment the x-control unit is configured to receive functional status data as control signals from said control unit 2a, 140, 200, 710, wherein the control data is based on processed user input data, to control servo motors to a predetermined position based on said functional status data by sending servo motor signals, thereby narrowing the area of interest of the patient exposed to the X-ray beam and to obtain functional status data indicative of the status of a servo motor by receiving servo motor signals and to send functional status data as status control signals to said first control unit 2a, 140, 200, 710. The x-control unit 713, the DAP chambers 231, the control unit 2a, 140, 200, 710 and the servo motors are communicatively coupled to each other, for instance by means of a cable or through wireless signal transmission.

Figure 16:
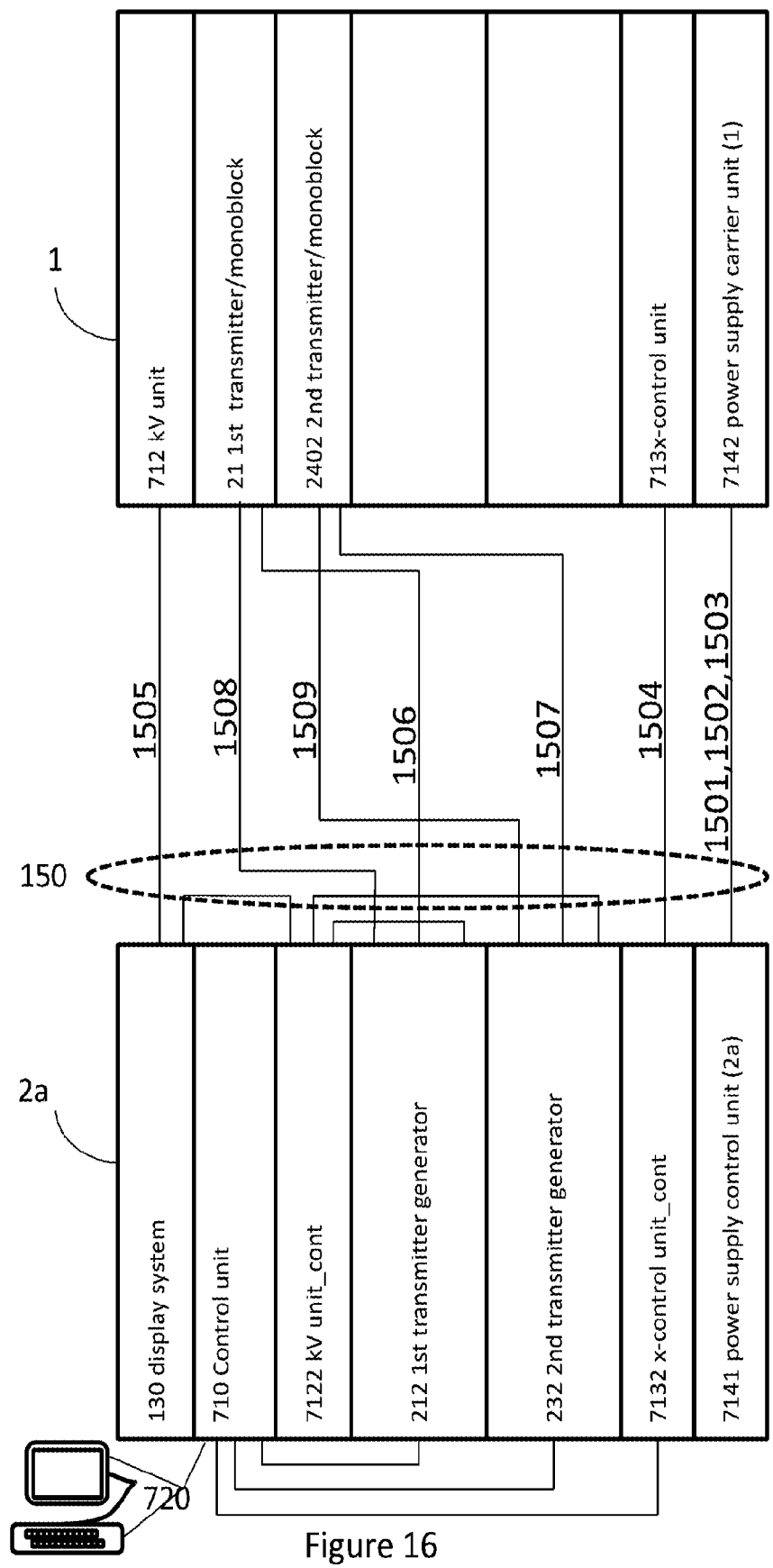
FIG. 16 shows an embodiment of a fluoroscopy system comprising a mobile X-ray system carrier communicatively coupled to a mobile control unit by a cable.

FIG. 16 shows another schematic view of an embodiment of a system comprising a cable 150 connecting the X-ray system carrier unit 1 with the control unit 2a, 140, 200, 710. The mains-connections 1501 protective earth (PE), 1502 line (L) and 1503 neutral (N) provides power from X-ray system carrier unit power supply 7142 to the control unit power supply 7141 or vice versa. The 1504 CAN bus connects the x-control unit 713 to x-control unit_cont 7132 and transfers functional status data in both directions, e.g. indicative of a predetermined position to control servo motors 740 to or DAP parameter values. The 1505 connects the kV unit 712 to the display system card 130 (not shown in the image) and transfers functional status data in both directions, e.g. indicative of captured X-ray images, target power of the transmitters 21, 23 in kV or mA values and activation timing of the transmitters. The 1506 $1^{st}$ transmitter control connects the first transmitter 21 to a $1^{st}$ transmitter generator unit 212 and transfers functional status data in both directions, e.g. indicative of detected errors in the transmitter/monoblock. The 1507 $2^{nd}$ transmitter control connects the second transmitter 23 to a transmitter generator unit 232 and transfers functional status data in both directions, e.g. indicative of detected errors. The 1508 $1^{st}$ transmitter high power supply connects the first transmitter 21 to a $1^{st}$ transmitter generator unit 212 and transfers high power to the first transmitter 21 or monoblock. The 1509 $2^{nd}$ transmitter high power supply connects the second transmitter 23 to a $2^{nd}$ transmitter generator unit 232 and transfers high power to the second transmitter 23 or monoblock. The $1^{st}$ transmitter generator unit 212 is further connected to the kV unit unit_cont 7122 and the control unit 2a, 140, 200, 710. The $2^{nd}$ transmitter generator unit 232 is further connected to the kV unit unit_cont 7122 and the control unit 2a, 140, 200, 710. In embodiments, the kV unit unit_cont 7122 is further connected to the display system 130. In embodiments, the x-control unit_cont 7132 is further communicatively connected to the control unit 2a, 140, 200, 710. In embodiments, the control unit 2a, 140, 200, 710 further comprises a control interface 720 configured to receive user input data as user indications from a user.

In one or more embodiments, a computer program product comprising computer readable code configured to, when executed in a processor, perform any or all of the method steps described herein.

In one or more embodiments, a non-transitory computer readable memory on which is stored computer readable code configured to, when executed in a processor, perform any or all of the method steps described herein.

A tangibly embodied computer-readable medium including executable code that, when executed, causes a control unit to perform any or all of the method steps described herein.

A tangibly embodied computer-readable medium including executable code that, when executed, causes a servo motor unit to perform any or all of the method steps described herein.

The invention claimed is:

1. A mobile digital fluoroscopy system comprising:
 a mobile X-ray system carrier unit comprising;
 a first and a second X-ray device each having a transmitter and a receiver, wherein said respective first and second X-ray devices are configured to enable X-ray imaging in mutually intersecting planes,
a kV unit; and
wherein said a mobile control unit is communicatively coupled to the mobile X-ray system carrier via a cable;
wherein said mobile control unit is configured to receive a first set of image data from said kV unit and sending a control signal to said kV unit upon completion of receiving of said image data;
wherein kV unit is configured to generate a synchronization signal to said transmitters and receivers and to send a second set of image data received from receivers to the mobile control unit.

2. The system of claim 1, wherein the synchronization signal is configured to control timing of the first and/or second transmitter to emit or not to emit X-ray energy based on said synchronization signal and to control timing of said first receiver and said second receiver to capture and send a second set of image data to said kV unit.

3. The system of claim 1, wherein said kV unit is further configured to receive image data from first receiver and said second receiver;
discarding image data received from said second receiver and only sending image data received from the first receiver to said mobile control unit; or;
discarding image data received from said first receiver and only sending image data received from the second receiver to said mobile control unit;
wherein discarding is based on predefined data parameters, indicative of at least an image discard pattern, retrieved from a memory communicatively coupled to said kV unit and/or functional status data in the form of user input data received from said control unit.

4. A method in a mobile digital fluoroscopy system comprising:
a mobile X-ray system carrier unit comprising;
a first and a second X-ray device each having a transmitter and a receiver, wherein said respective first and second X-ray devices are configured to enable X-ray imaging in mutually intersecting planes,
a kV unit; and;
wherein said a mobile control unit is communicatively coupled to the mobile X-ray system carrier via a cable, the method comprising:
receiving a first set of image data, by mobile control unit, from said kV unit,
sending, by mobile control unit, a control signal to said kV unit upon completion of receiving of said image data,
generating a synchronization signal to said transmitters and receivers;
sending image data received from receivers to the mobile control unit.

5. The method of claim 4, wherein the synchronization signal is configured to control timing of the first and/or second transmitter to emit/not to emit X-ray energy based on said synchronization signal and to control timing of said first receiver and said second receiver to capture and send a second set of image data to said kV unit.

6. The method of claim 4, further comprising:
receiving, by said kV unit, image data from first receiver and said second receiver;
discarding image data received from said second receiver and only sending image data received from the first receiver to said mobile control unit; or;
discarding image data received from said first receiver and only sending image data received from the second receiver to said mobile control unit;
wherein discarding is based on predefined data parameters, indicative of at least an image discard pattern, retrieved from a memory communicatively coupled to said kV unit and/or functional status data in the form of user input data received from said control unit.

7. A computer program product comprising non-transitory computer readable code configured to, when executed in a processor, perform at least one of the functions according to claim 1.

8. A non-transitory machine readable medium on which is stored non-transitory computer readable code configured to, when executed in a processor, perform at least one of the functions according to claim 1.

* * * * *